United States Patent
Brooks et al.

(10) Patent No.: US 10,957,858 B2
(45) Date of Patent: *Mar. 23, 2021

(54) ORGANIC ELECTROLUMINESCENT MATERIALS AND DEVICES

(71) Applicant: Universal Display Corporation, Ewing, NJ (US)

(72) Inventors: Jason Brooks, Philadelphia, PA (US); Chuanjun Xia, Lawrenceville, NJ (US); Raymond Kwong, Plainsboro, NJ (US); James Fiordeliso, Morrisville, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 150 days.

This patent is subject to a terminal disclaimer.

(21) Appl. No.: 16/385,083

(22) Filed: Apr. 16, 2019

(65) Prior Publication Data
US 2019/0245147 A1    Aug. 8, 2019

Related U.S. Application Data

(63) Continuation of application No. 15/449,497, filed on Mar. 3, 2017, now Pat. No. 10,312,450, which is a
(Continued)

(51) Int. Cl.
*H01L 51/50* (2006.01)
*H01L 51/00* (2006.01)
(Continued)

(52) U.S. Cl.
CPC ......... *H01L 51/0054* (2013.01); *C07C 15/38* (2013.01); *C07D 307/91* (2013.01);
(Continued)

(58) Field of Classification Search
None
See application file for complete search history.

(56) References Cited

U.S. PATENT DOCUMENTS 4,769,292 A    9/1988 Tang et al.
5,061,569 A    10/1991 VanSlyke et al.
(Continued)

FOREIGN PATENT DOCUMENTS

EP    0650955    5/1995
EP    1725079    11/2006
(Continued)

OTHER PUBLICATIONS

Brinen, "ESR and Luminescence Studies of Substituted Triphenylenes, Excited State Resonance Interactions" Journal of Luminescence 5 (1972) 73-83.
(Continued)

*Primary Examiner* — Gregory D Clark
(74) *Attorney, Agent, or Firm* — Duane Morris LLP

(57) ABSTRACT

A compound having the structure of Formula I

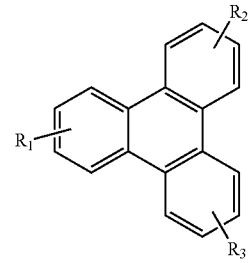

is disclosed. In the structure of Formula I, each of $R_1$, $R_2$, and $R_3$ is independently a hydrogen, a non-fused aryl group
(Continued)

having one meta-substituent, or a non-fused heteroaryl six-membered ring having one or more meta-substituents; each meta-substituent is a non-fused aryl or non-fused heteroaryl six-membered ring optionally substituted with further substituents selected from the group consisting of non-fused aryl groups, non-fused heteroaryl groups, and alkyl groups; and at least one of $R_1$, $R_2$, and $R_3$ is a non-fused aryl having one meta-substituent or a heteroaryl six-membered ring having at least one meta-substituent, wherein each meta-substituent is a non-fused aryl or non-fused heteroaryl group further substituted with a chain of at least two non-fused aryl or non-fused heteroaryl groups. The compounds may be useful in phosphorescent organic light emitting devices.

9 Claims, 12 Drawing Sheets

Related U.S. Application Data continuation of application No. 14/491,280, filed on Sep. 19, 2014, now Pat. No. 9,590,180, which is a continuation of application No. 14/135,191, filed on Dec. 19, 2013, now Pat. No. 9,608,206, which is a continuation of application No. 12/865,628, filed as application No. PCT/US2008/072452 on Aug. 7, 2008, now Pat. No. 8,652,652.

(60) Provisional application No. 60/963,944, filed on Aug. 8, 2007, provisional application No. 61/017,506, filed on Dec. 28, 2007.

(51) Int. Cl.
*C07C 15/38* (2006.01)
*C07D 307/91* (2006.01)
*C07D 333/76* (2006.01)
*C07D 409/04* (2006.01)
*C09K 11/06* (2006.01)
*H05B 33/14* (2006.01)
*C09B 57/00* (2006.01)
*C09K 11/02* (2006.01)

(52) U.S. Cl.
CPC ......... *C07D 333/76* (2013.01); *C07D 409/04* (2013.01); *C09B 57/00* (2013.01); *C09K 11/025* (2013.01); *C09K 11/06* (2013.01); *H01L 51/004* (2013.01); *H01L 51/0061* (2013.01); *H01L 51/0085* (2013.01); *H01L 51/5004* (2013.01); *H05B 33/14* (2013.01); *C07C 2603/42* (2017.05); *C09K 2211/1007* (2013.01); *C09K 2211/1011* (2013.01); *H01L 51/0059* (2013.01); *H01L 51/0081* (2013.01); *H01L 51/5016* (2013.01); *H01L 51/5024* (2013.01); *H01L 2251/552* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,310,360 B1 | 10/2001 | Forrest et al. |
| 6,337,102 B1 | 1/2002 | Forrest et al. |
| 6,468,819 B1 | 10/2002 | Kim et al. |
| 6,528,187 B1 | 3/2003 | Okada |
| 6,548,956 B2 | 4/2003 | Forrest et al. |
| 6,576,134 B1 | 8/2003 | Agner |
| 6,602,540 B2 | 8/2003 | Gu et al. |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,652,652 B2 | 2/2014 | Brooks et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2002/0182441 A1 | 12/2002 | Lamansky et al. |
| 2003/0072964 A1 | 4/2003 | Kwong et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0057426 A1 | 3/2006 | Itoh |
| 2006/0088728 A1 | 4/2006 | Kwong et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0134780 A1 | 5/2009 | Ono et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| JP | 2003282270 | 10/2003 |
| JP | 200511610 | 1/2005 |

(56) References Cited

FOREIGN PATENT DOCUMENTS

| | | |
|---|---|---|
| JP | 2005276801 | 10/2005 |
| JP | 2007123392 | 5/2007 |
| JP | 2007254297 | 10/2007 |
| JP | 2008074939 | 4/2008 |
| JP | 2008150365 | 7/2008 |
| JP | 2008214306 | 9/2008 |
| JP | 2008214307 | 9/2008 |
| JP | 2008247895 | 10/2008 |
| WO | 2009100991 | 8/2000 |
| WO | 01/39234 | 5/2001 |
| WO | 02/02714 | 1/2002 |
| WO | 02015654 | 2/2002 |
| WO | 2002074015 | 9/2002 |
| WO | 30340257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006128800 | 12/2006 |
| WO | 2006130598 | 12/2006 |
| WO | 2006132173 | 12/2006 |
| WO | 2007002683 | 1/2007 |
| WO | 2007004380 | 1/2007 |
| WO | 2007043357 | 4/2007 |
| WO | 2007063754 | 6/2007 |
| WO | 2007063796 | 6/2007 |
| WO | 2007108362 | 9/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021107 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |

OTHER PUBLICATIONS

Gary L. Miessler and Donald A. Tarr, "Inorganic Chemistry" (2nd Edition), Prentice Hall (1998).
Pyridine and Pyridine Derivatives, 1979, Kirk-Othmer Encyclopedia of Chemical Technology, 4th Edition, p. 1.
Meta-, Ortho-, Para-, 1979, The Great Soviet Encyclopedia, p. 1.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosohorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide,"SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphores Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129(2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting a Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

(56) References Cited

OTHER PUBLICATIONS

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing $N^{\wedge}C^{\wedge}N$-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II Phosphorescent Emitters,"0 Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

US 10,957,858 B2

ORGANIC ELECTROLUMINESCENT MATERIALS AND DEVICES

CROSS REFERENCE TO RELATED APPLICATIONS

This application is a continuation of copending U.S. application Ser. No. 15/449,497, filed Mar. 3, 2017, which is a continuation of U.S. application Ser. No. 14/491,280, filed Sep. 19, 2014, which issued as U.S. Pat. No. 9,590,180, which is a continuation of U.S. application Ser. No. 14/135,191, filed Dec. 19, 2013, which issued as U.S. Pat. No. 9,608,206, which is a continuation of U.S. application Ser. No. 12/865,628, filed Dec. 30, 2010, which issued as U.S. Pat. No. 8,652,652, which is a National Stage Entry of International Application PCT/US2008/072452, filed Aug. 7, 2008, which claims priority to U.S. Provisional Application Ser. No. 60/963,944, filed Aug. 8, 2007, and U.S. Provisional Application Ser. No. 61/017,506, filed Dec. 28, 2007, the disclosures of which are herein expressly incorporated by reference in their entirety.

JOINT RESEARCH AGREEMENTS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and specifically to phosphorescent organic materials used in such devices. More specifically, the present invention relates to triphenylene compounds incorporated into OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

SUMMARY OF THE INVENTION

The present invention is directed to triphenylene compounds useful in phosphorescent organic light emitting diodes. Specific examples include multi-aryl-substituted triphenylenes. A preferred group of compounds are triphenylenes that are substituted with a non-fused aryl group having one or more meta-substituents, where each meta-substituent is a non-fused aryl group optionally substituted with further substituents selected from the group consisting of non-fused aryl groups and alkyl groups. Some high triplet energy analogs are expected to work with deep blue phosphorescent dopants.

Additional preferred compounds are triphenylenes that are substituted with a non-fused heteroaryl group having one or more meta-substituents, where each meta-substituent is a non-fused aryl or heteroaryl group optionally substituted with further substituents selected from the group consisting of non-fused aryl groups, non-fused heteroaryl groups, and alkyl groups.

In a preferred aspect of the invention, opto-electronic materials containing a single triphenylene chromophore are demonstrated as a useful class of host materials and enhancement layer materials. These compounds have shown long device lifetime as hosts and blockers for devices doped with red and green phosphorescent emissive materials. When used as phosphorescent host materials, single triphenylene containing compounds have demonstrated less red-shifting of the dopant emission when compared to a comparative example host that contains two triphenylene chromophores. This optical effect may allow for devices to be fabricated with more saturated color. An additional advantage of single triphenylene containing derivatives is that they can be easier to synthesize and can be more soluble when compared to many derivatives that contain two chromophores. The improved solubility of these materials can be helpful with purification and also can allow for these materials to be used as host materials for solution processed or ink jet printed devices.

An emissive layer in an organic light emitting device is provided. The emissive layer includes a phosphorescent material and a triphenylene compound. Preferably the triphenylene compound has an energy gap between the HOMO and the LUMO energy levels that is larger than the energy gap between the HOMO and the LUMO energy levels of the phosphorescent material.

In a preferred embodiment, the triphenylene compound in the emissive layer has an energy gap between its HOMO energy level and its LUMO energy level of at least about 1.8 eV.

In another embodiment, the triphenylene compound has a highest occupied molecular orbital that is lower than the highest occupied molecular orbital of the phosphorescent material.

In another embodiment, the triphenylene compound has a lowest unoccupied molecular orbital that is higher than the lowest unoccupied molecular orbital of the phosphorescent material.

In one embodiment, the emissive layer comprises a phosphorescent material and a triphenylene compound wherein the triphenylene compound has the formula:

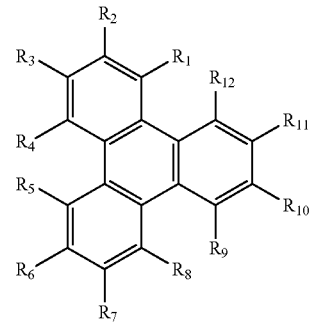

Where each $R_1$, $R_2$, $R_3$, $R_4$, $R_5$, $R_6$, $R_7$, $R_8$, $R_9$, $R_{10}$, $R_{11}$ and $R_{12}$ is independently H or a substituent selected from the group consisting of aryl, substituted aryl, heteroaryl, substituted heteroaryl, alkyl, arylkyl heteroalkyl, alkenyl, and alkynyl and wherein the triphenylene compound has at least two substituents. Preferably, the triphenylene compound has a molecular weight of less than 1400. In some preferred embodiments, at least one of $R_1$, $R_2$, $R_3$, $R_4$, $R_5$, $R_6$, $R_7$, $R_8$, $R_9$, $R_{10}$, $R_{11}$ and $R_{12}$ is selected from aryl and substituted aryl. In another embodiment, each of $R_2$, $R_3$, $R_6$, $R_7$, $R_{10}$, and $R_{11}$ is selected from aryl and substituted aryl and in yet another embodiment, each of $R_2$, $R_3$, $R_6$, $R_7$, $R_{10}$, and $R_{11}$ is selected from aryl and substituted aryl and $R_2$, $R_3$, $R_6$, $R_7$, $R_{10}$, and $R_{11}$ are all the same.

A general structure that describes the single triphenylene chromophore aspect of the invention is shown below.

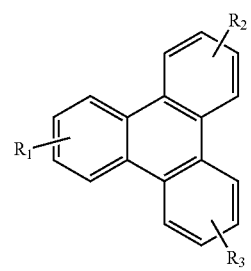

where $R_1$, $R_2$, $R_3$ are independently H or aryl groups with the exception of triphenylene and at least one of $R_1$, $R_2$, $R_3$ is not H. $R_1$, $R_2$, $R_3$ may also independently be H, aryl groups, or heteroaryl groups with the exception of triphenylene and at least one of $R_1$, $R_2$, $R_3$ is not H.

In one embodiment, each of $R_1$, $R_2$, and $R_3$ is independently a hydrogen, a non-fused aryl group or a non-fused heteroaryl group having one or more meta-substituents. Each meta-substituent is a non-fused aryl or heteroaryl group optionally_substituted with further substituents selected from the group consisting of non-fused aryl groups, non-fused heteroaryl groups, and alkyl groups, and wherein at least one of R₁, R₂, and R₃ is a non-fused aryl or heteroaryl group having at least one meta-substituent that is a non-fused aryl or heteroaryl group further substituted with one or more non-fused aryl or heteroaryl groups.

An organic electroluminescent device is also provided. A preferred device comprises an anode, a cathode, and an emissive layer comprising a triphenylene material and a phosphorescent material between the anode and the cathode. The triphenylene material may have the formula:

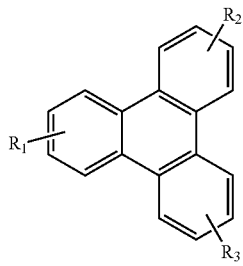

where R₁, R₂, R₃ are independently H or aryl groups with the exception of Triphenylene and at least one of R₁, R₂, R₃ is not H. R₁, R₂, R₃ may also independently be H, aryl groups, or heteroaryl groups with the exception of triphenylene and at least one of R₁, R₂, R₃ is not H.

In one embodiment of the organic electroluminescent device, each of R₁, R₂, and R₃ is independently a hydrogen, a non-fused aryl group or a non-fused heteroaryl group having one or more meta-substituents. Each meta-substituent is a non-fused aryl or heteroaryl group optionally substituted with further substituents selected from the group consisting of non-fused aryl groups, non-fused heteroaryl groups, and alkyl groups, and wherein at least one of R₁, R₂, and R₃ is a non-fused aryl or heteroaryl group having at least one meta-substituent that is a non-fused aryl or heteroaryl group further substituted with one or more non-fused aryl or heteroaryl groups.

Also provided is an organic electroluminescent device comprising an anode, a cathode, and an emissive layer between the anode and the cathode, the emissive layer comprising a phosphorescent material and a compound having a repeat unit, the repeat unit containing a triphenylene moiety.

DETAILED DESCRIPTION

Figure 1:
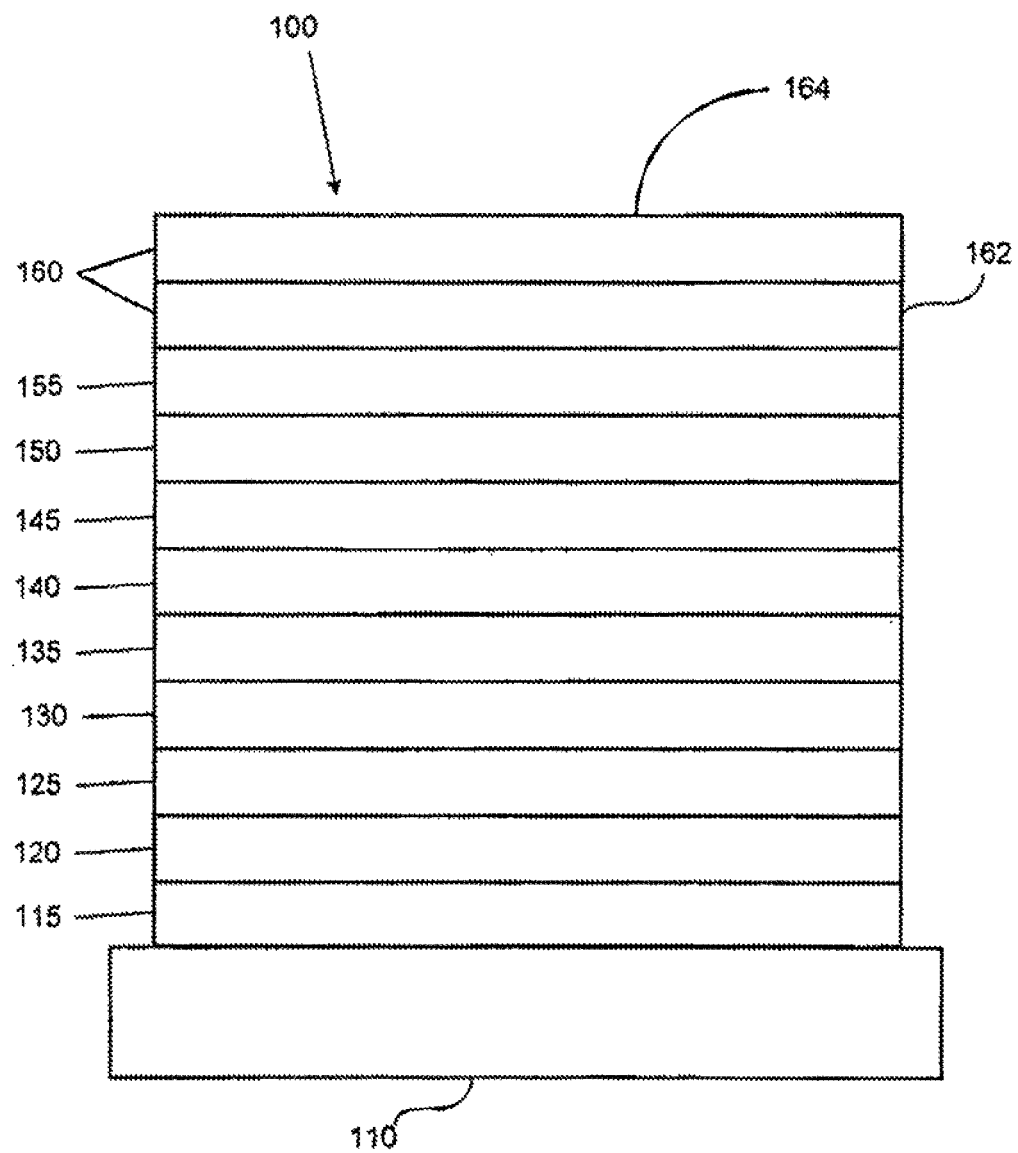
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organo-metallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tarr, Prentice Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice, organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials in OLEDs include $Alq_3$, CBP and mCP. Examples of emissive and host materials in OLEDs are disclosed in U.S. Pat. No. 6,303,238 to Thompson et al., which is incorporated by reference in its entirety. In the present invention, preferred host materials include triphenylene complexes. Triphenylene compounds are useful materials in other applications in OLEDs such as electron transporting materials as described in US US20050025993. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the luminescent properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels directly involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. Alq$_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2, and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one of skill in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
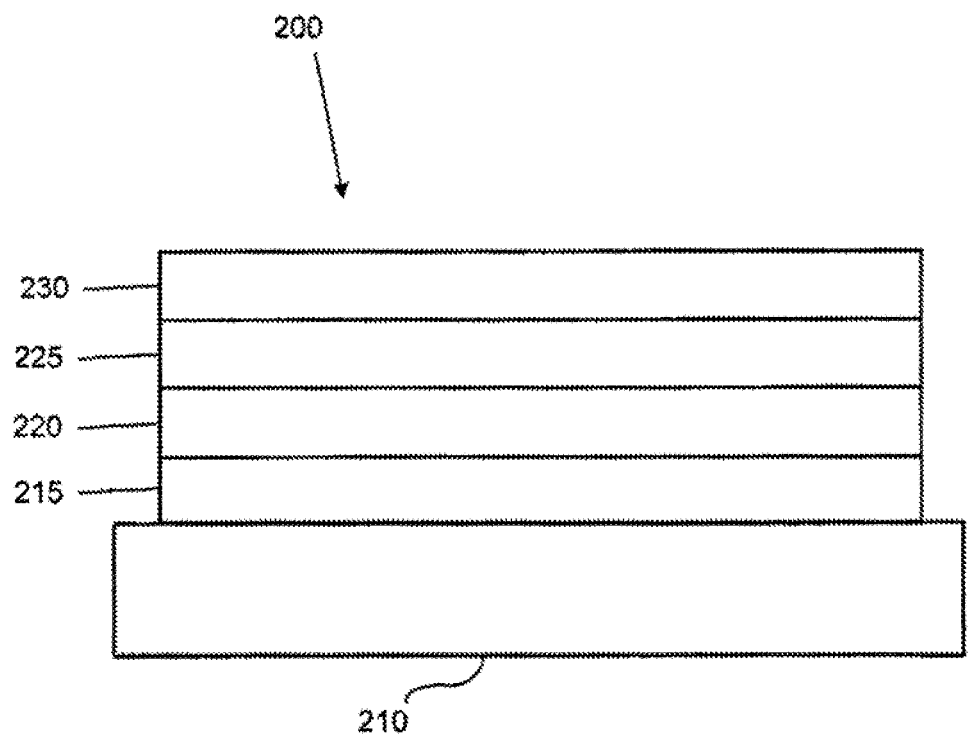
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, $C(O)R$, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, $C(O)R$, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, $C(O)R$, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, $C(O)R$, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring groups and polycyclic ring systems. The polycyclic rings may have two or more rings in which two atoms are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to four heteroatoms, for example, pyrrole, furan, thiophene, imidazole, oxazole, thiazole, triazole, tetrazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

The present invention is directed to an organic emissive layer comprising a phosphorescent material and a triphenylene compound, as well as a device including such an emissive layer. Specific triphenylene compounds are also provided. In preferred embodiments of the invention, the organic emissive layer includes a phosphorescent material and a triphenylene compound, optionally substituted. The substituents may be the same or different and each is selected from the group consisting of alkyl, aryl, substituted aryl, heteroaryl, alkenyl, alkynyl, and heteroalkyl. Particularly preferred are triphenylene compounds having a molecular weight of less than 1400 that can be evaporated at vacuum without decomposition. High efficiency and lifetime are demonstrated by devices fabricated according to the present invention. The high triplet energy of triphenylene renders triphenylene compounds particularly suitable as hosts or co-hosts for use with deep blue phosphorescent dopants.

Triphenylene is a polyaromatic hydrocarbon with a high triplet energy and a relatively small energy difference between the first singlet and first triplet levels. This would indicate that triphenylene has relatively easily accessible HOMO and LUMO levels compared to other aromatic compounds with similar triplet energy (e.g., biphenyl). The advantage of using triphenylene and its derivatives as hosts is that it can accommodate red, green and even blue phosphorescent dopants to give high efficiency without energy quenching.

Preferably the triphenylene compound in the present invention has an energy gap between the HOMO and the LUMO energy levels that is larger than the energy gap between the HOMO and the LUMO energy levels of the phosphorescent material.

In a preferred embodiment, the triphenylene compound in the present invention has an energy gap between its HOMO energy level and its LUMO energy level of at least about 1.8 eV.

In another embodiment, the triphenylene compound has a highest occupied molecular orbital that is lower than the highest occupied molecular orbital of the phosphorescent material.

In another embodiment, the triphenylene compound has a lowest unoccupied molecular orbital that is higher than the lowest unoccupied molecular orbital of the phosphorescent material.

In one aspect, the present invention describes a new class of hosts and enhancement layers based on single triphenylene containing materials that allow for highly efficient phosphorescent devices with long device lifetime and saturated dopant emission. In some instances, previous host and enhancement materials based on a triphenylene chromophore containing two triphenylenes have been found to be less soluble than materials that contain a single triphenylene chromophore. In some instances, when materials that contain two triphenylenes are used as hosts, they have been observed to red-shift the emission spectra of the dopant. In comparison, single triphenylene compounds described herein when used as phosphorescent hosts do not red shift the emission spectra of the dopant. This is an advantage that allows for more saturated dopant color. In addition, the new family of single triphenylene substituted materials may be easier to synthesize because only one triphenylene coupling reaction is required. These materials have demonstrated improved solubility which may be useful for column chromatography purification. Finally, the improved solubility can allow for these materials to be employed in devices that are solution processed.

In the single Triphenylene-containing host and enhancement materials described herein, the Triphenylene may be substituted with aryl groups. In particular preferred embodiments, the aryl groups are substituted in the meta positions to limit direct conjugation and maintain a high triplet energy. It is believed that more than 4 linear para-substituted phenyl rings, including the rings of the triphenylene, will be enough to lower the triplet energy to quench the phosphorescent emission of the dopant. Meta substituted phenylene chains or meta branched phenyl rings may help lower symmetry, decrease crystalinity and improve solubility.

The single triphenylene-containing host and enhancement materials described herein may also be contain a triphenylene that is substituted with heteroaryl groups. In particular preferred embodiments, the heteroaryl groups are substituted in the meta positions to limit direct conjugation and maintain a high triplet energy. For the reasons discussed above, it is believed that meta-substituented heteroaryl chains maintain a high triplet energy and may help lower symmetry, decrease crystalinity and improve solubility.

A general structure that describes the single triphenylene chromophore aspect of the invention is shown below:

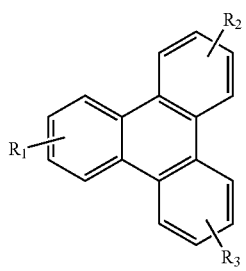

Where $R_1$, $R_2$, $R_3$ are independently H or non-fused aryl groups and at least one of $R_1$, $R_2$, $R_3$ is not H. Preferably, each of $R_1$, $R_2$, and $R_3$ is independently a hydrogen or a non-fused aryl group having one or more meta-substituents, where at least one of $R_1$, $R_2$, and $R_3$ is not hydrogen, and where each meta-substituent is a non-fused aryl group optionally substituted with further substituents selected from the group consisting of non-fused aryl groups and alkyl groups.

Additionally, $R_1$, $R_2$, $R_3$ are independently H, non-fused aryl groups, or non-fused heteroaryl groups and at least one of $R_1$, $R_2$, $R_3$ is not H. Preferably, each of $R_1$, $R_2$, and $R_3$ is independently a hydrogen or a non-fused aryl or heteroaryl group having one or more meta-substituents, where at least one of $R_1$, $R_2$, and $R_3$ is not hydrogen, and where each meta-substituent is a non-fused aryl or heteroaryl group optionally substituted with further substituents selected from the group consisting of non-fused aryl groups, non-fused heteroaryl groups, and alkyl groups.

Additional structures that describe the single triphenylene chromophore aspect of the invention are shown below where $R'_1$, $R'_2$, $R'_3$, $R'_4$, $R'_5$, $R'_6$ are aryl groups with the exception of Triphenylene:

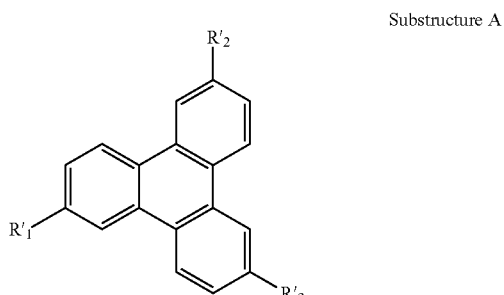

Substructure A

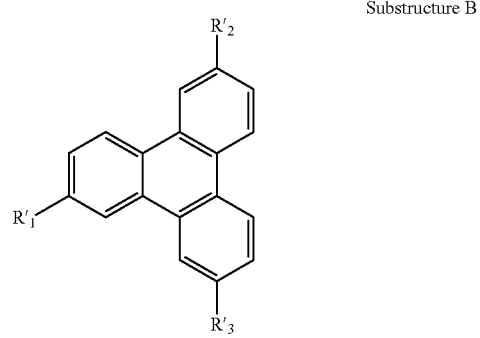

Substructure B

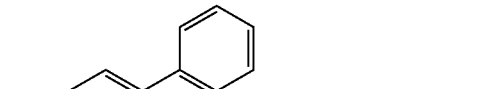

Substructure C

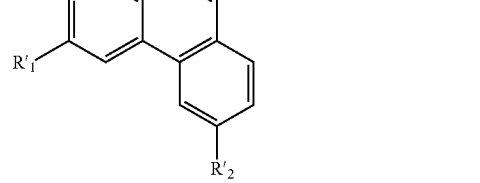

Substructure D

Substructure E
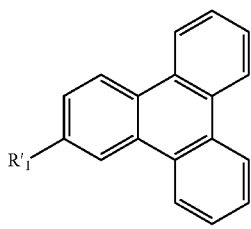
Substructure F
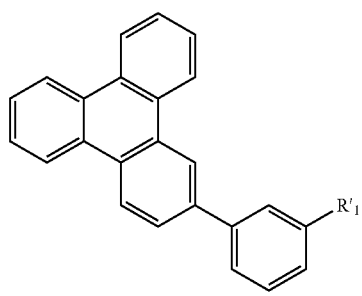
Substructure G
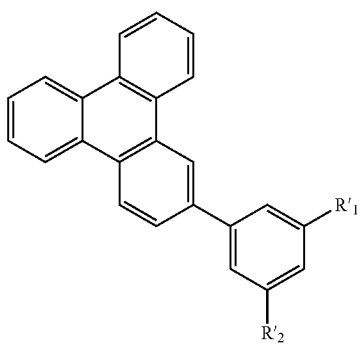
Substructure H
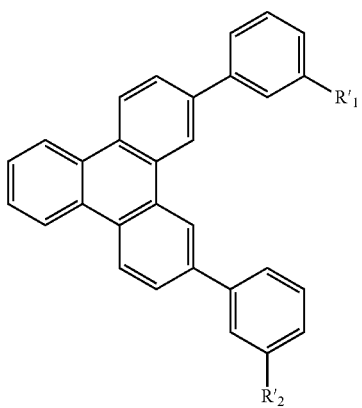
Substructure I
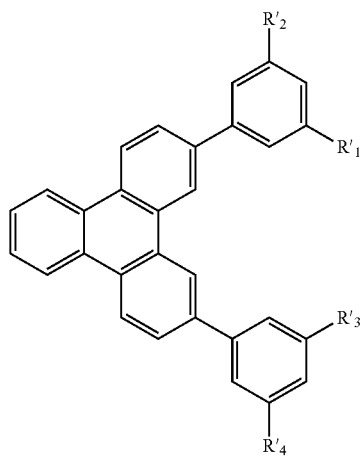
Substructure J
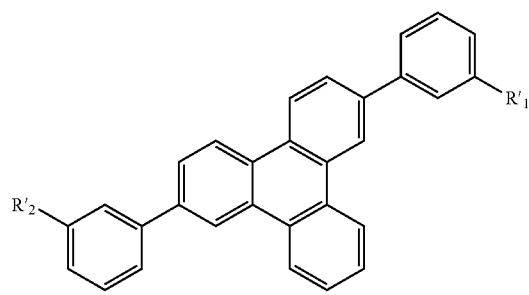
Substructure K
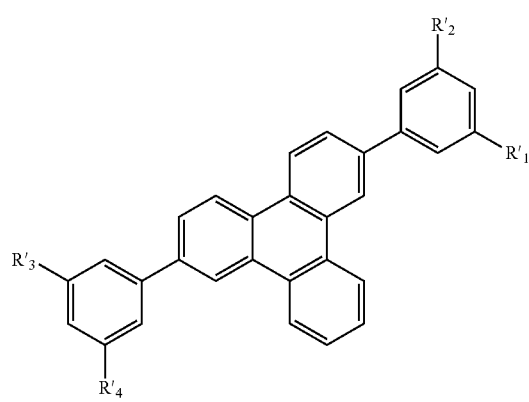

Substructure L
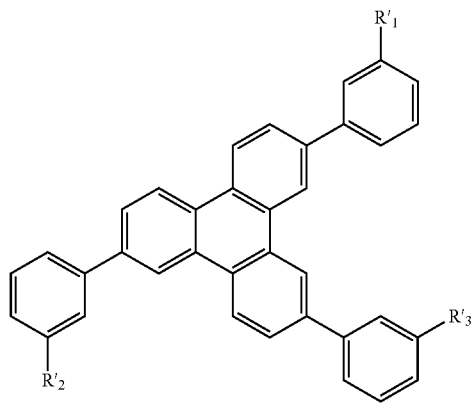
Substructure M
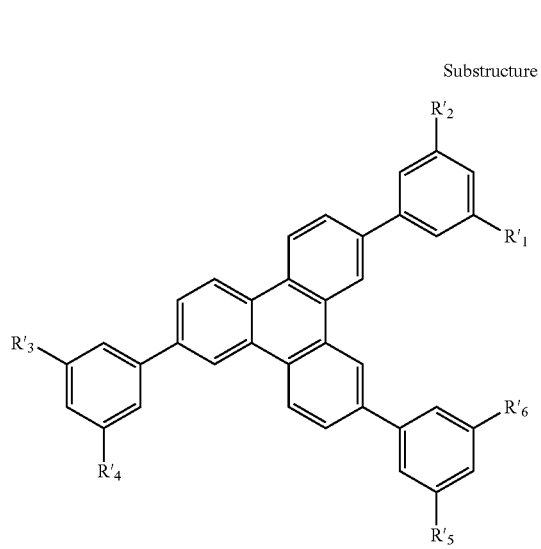
Substructure N
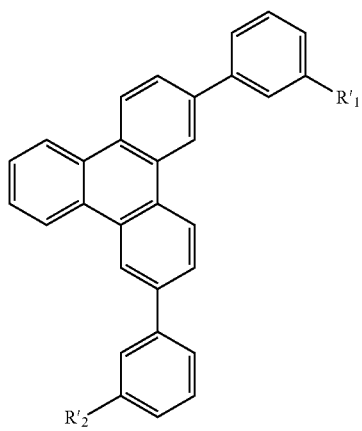
Substructure O
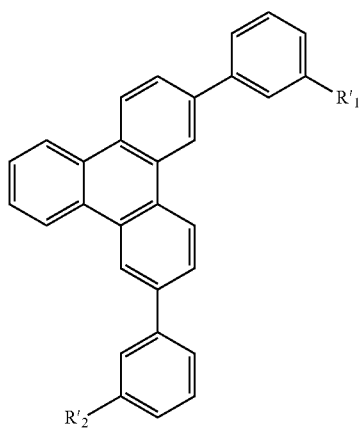
Where $R'_1$, $R'_2$, $R'_3$, $R'_4$, $R'_5$, $R'_6$ of Substructures A-O are aryl or heteroaryl groups with the exception of Triphenylene.
Specific examples that have been synthesized and demonstrate the single triphenylene chromophore aspect of the invention are shown below:
Compound 1
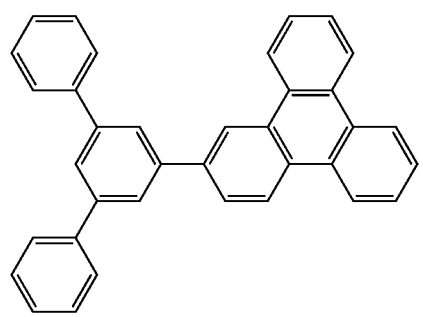
Compound 2
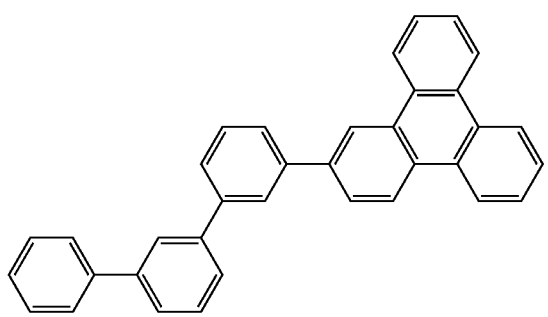

-continued
Compound 3
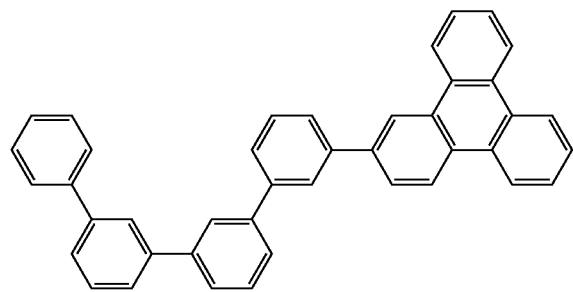
Compound 4
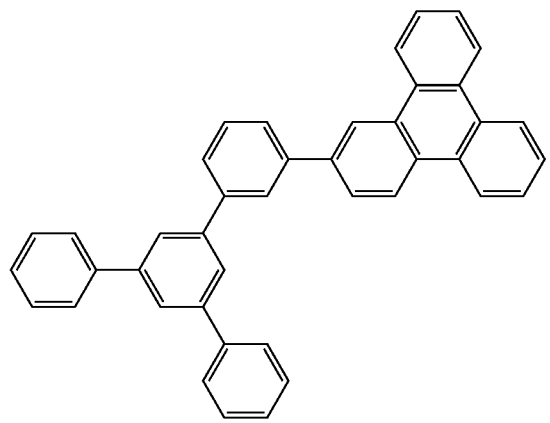
Compound 5
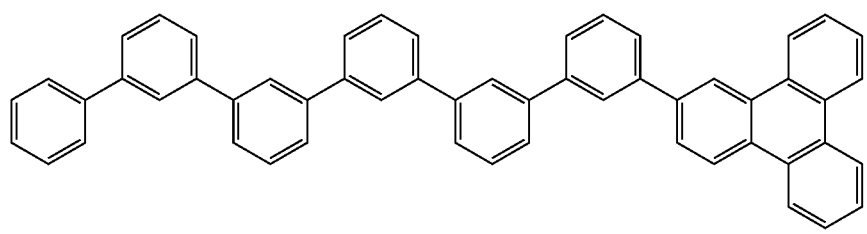
Compound 6
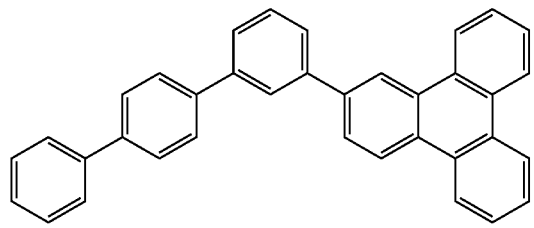
Compound 7
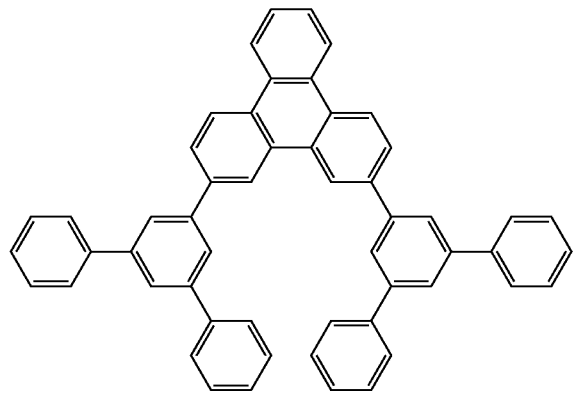
Compound 8
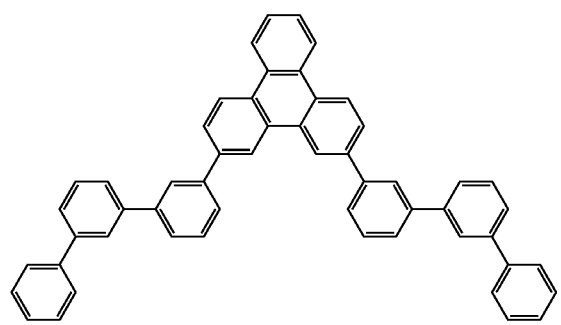
Compound 9
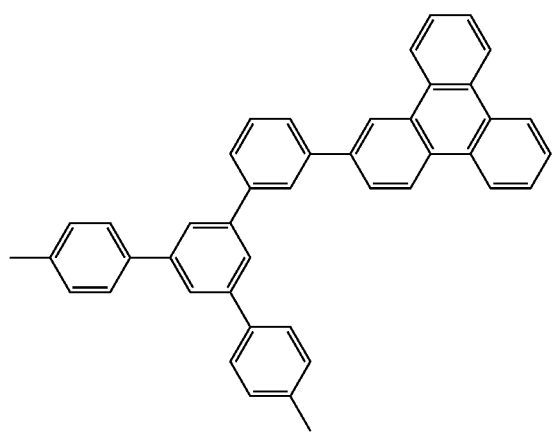

-continued
Compound 10
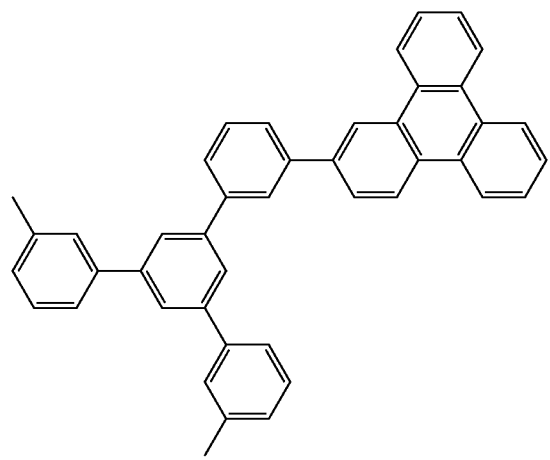
Compound 11
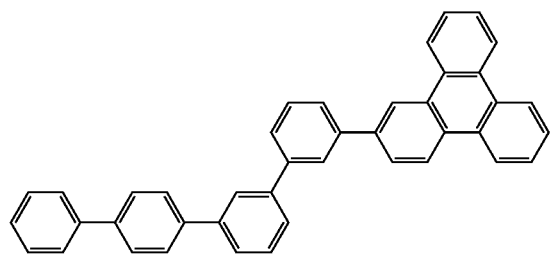
Compound 12
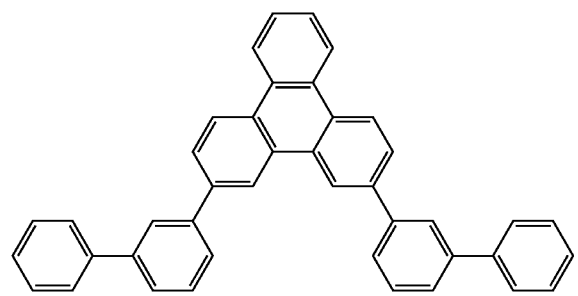
These materials are found to be more soluble compared to comparative examples 1 and 2, that contain two triphenylene chromophores.
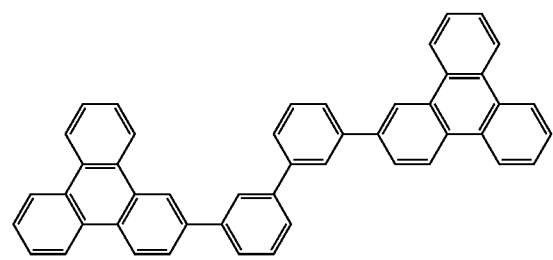 [SMILES: c1cc(-c2cccc(-c3ccc4c5ccccc5c5ccccc5c4c3)c2)cc(-c2ccc3c4ccccc4c4ccccc4c3c2)c1]
COMPARATIVE EXAMPLE 1
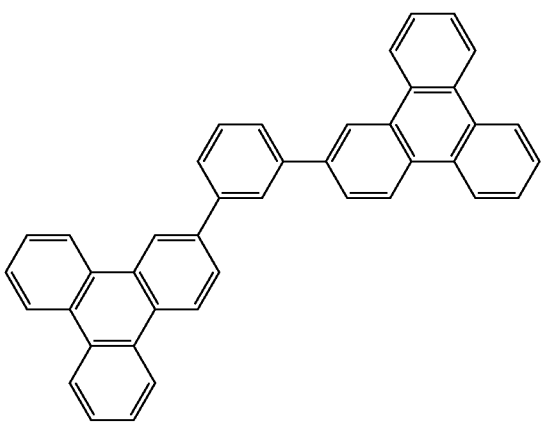 [SMILES: c1cc(-c2ccc3c4ccccc4c4ccccc4c3c2)cc(-c2ccc3c4ccccc4c4ccccc4c3c2)c1]

COMPARATIVE EXAMPLE 2

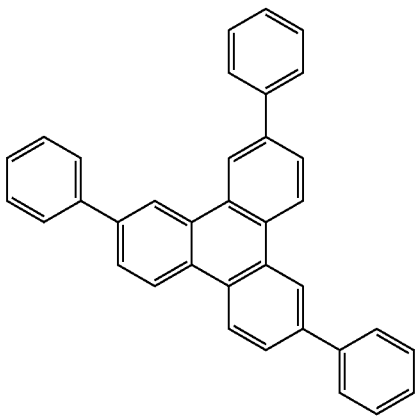 [SMILES: c1ccc(-c2ccc3c4ccc(-c5ccccc5)cc4c4cc(-c5ccccc5)ccc4c3c2)cc1]

COMPARATIVE EXAMPLE 3

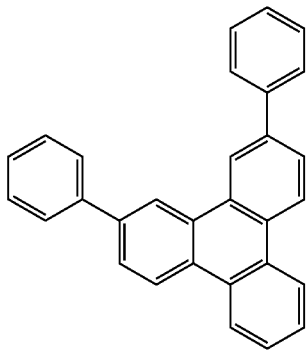 [SMILES: c1ccc(-c2ccc3c4ccccc4c4ccc(-c5ccccc5)cc4c3c2)cc1]

COMPARATIVE EXAMPLE 4

Figure 3:
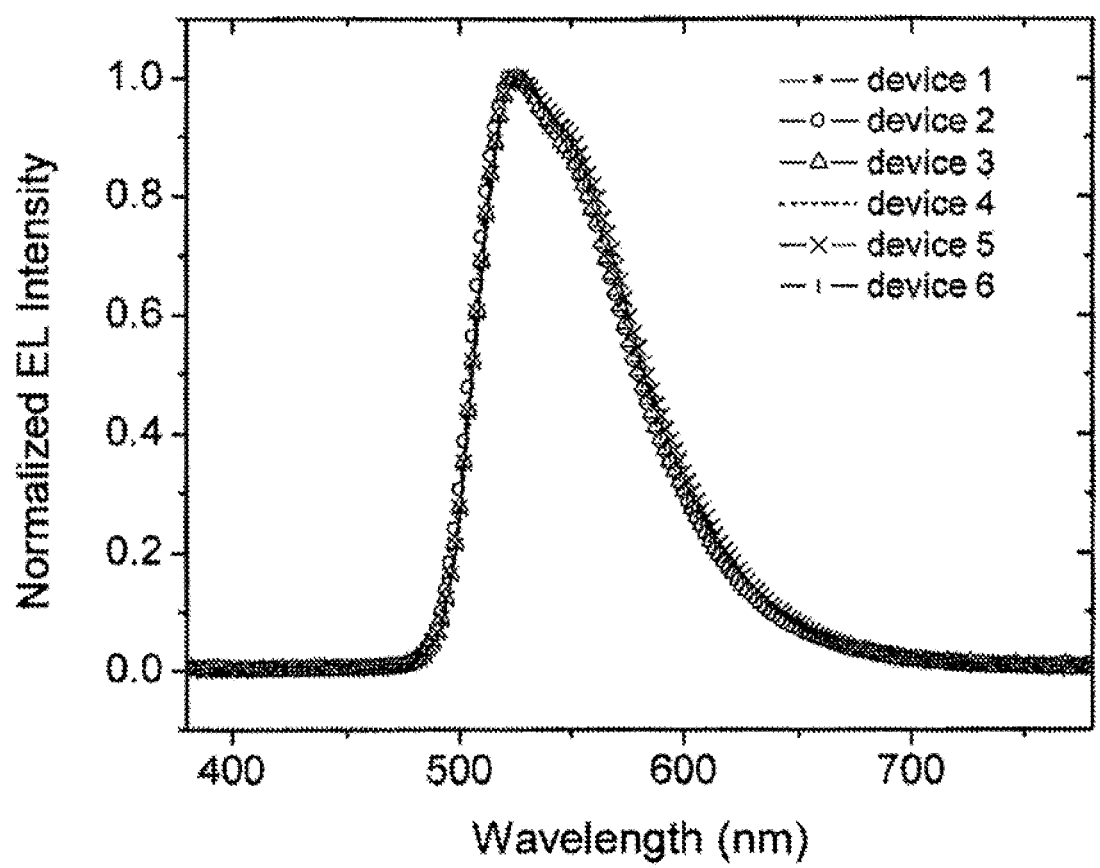
FIG. 3 shows the EL spectra for devices 1-6.
Figure 4:
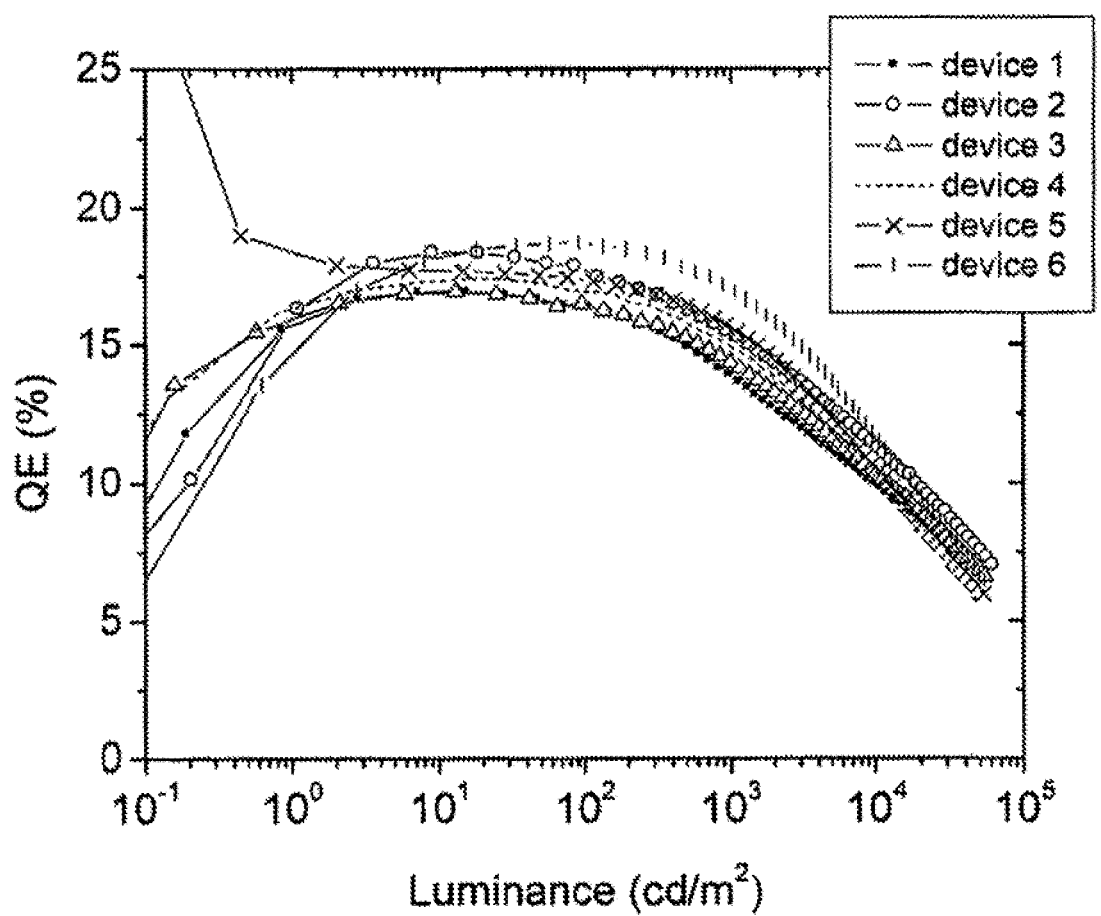
FIG. 4 shows quantum efficiency versus luminance for devices 1-6.
Figure 6:
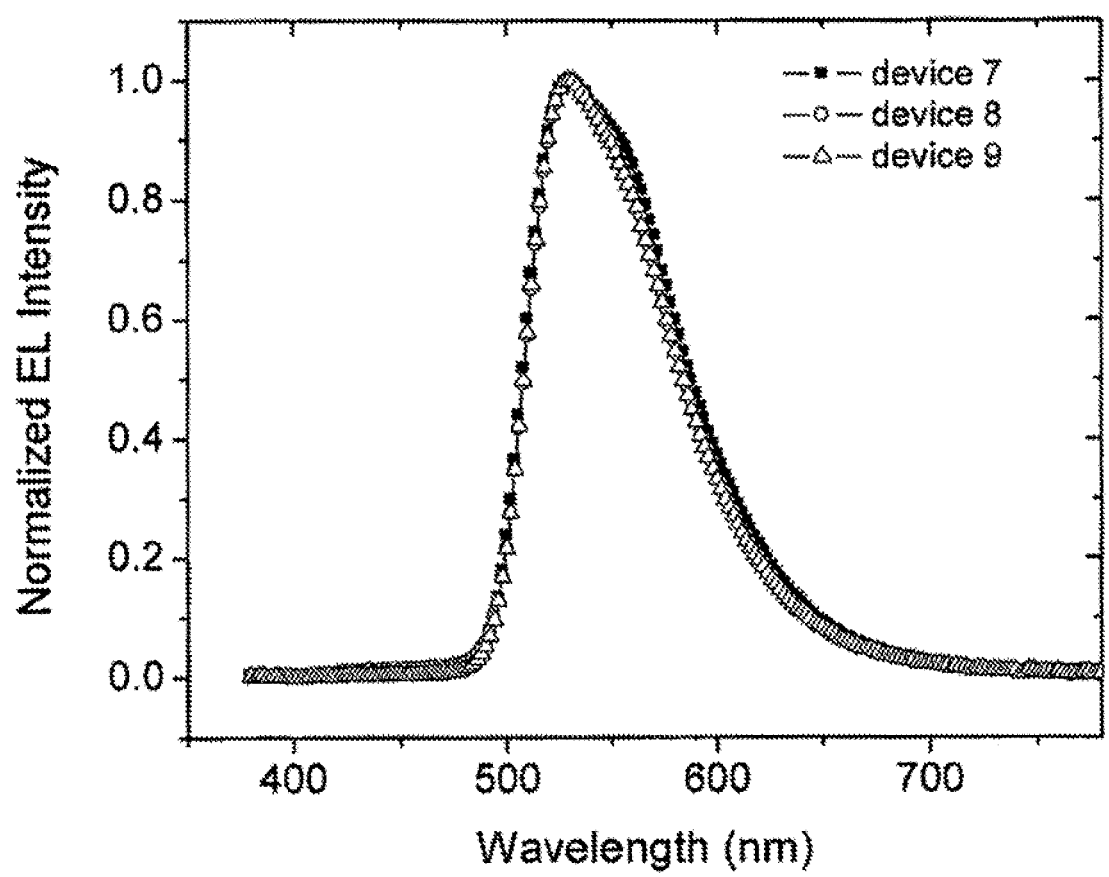
FIG. 6 shows the EL spectra for device 7-9.

VTE devices were fabricated with compounds 1, 2, 3, 4, 7, 8, 11 and 12. These materials were found to be stable as hosts and as enhancement layers. In addition when used as hosts for green phosphorescent dopants, compounds 1, 2, 3, 4, and 11, based on substructures G and F, were found to have significantly less red shifting of the emission of the green dopant compared to comparative example 1 and 2 as demonstrated by the CIE coordinates given in Table 1 and the EL spectra shown in FIGS. 3 and 6. In addition, compounds 7 and 8, based on substructures H and I were also found to have less red shifting compared to comparative example 1 as shown by the CIE coordinates in Table 1, but less so than the previously described examples. The color shifting effect of the host is important tool for designing device structures that provide more saturated green emission. The device data demonstrates that single triphenylene containing hosts materials offer advantages with respect to the CIE coordinates compared to two triphenylene containing comparative examples. In addition, compounds 1, 2, 4, 5, and 8 are very soluble in organic solvent and were used as phosphorescent hosts in solution processed devices. It is believed in these examples that meta substituted aryl rings can help reduce symmetry and improve solubility. Data for solution processed devices using single triphenylene containing materials as hosts is shown in Table 2. In comparison, the two triphenylene containing comparative examples 1 and 2 are not soluble enough for solution processing. Therefore, single triphenylene containing materials can have considerable advantages in terms of solubility and processibility.

Figure 7:
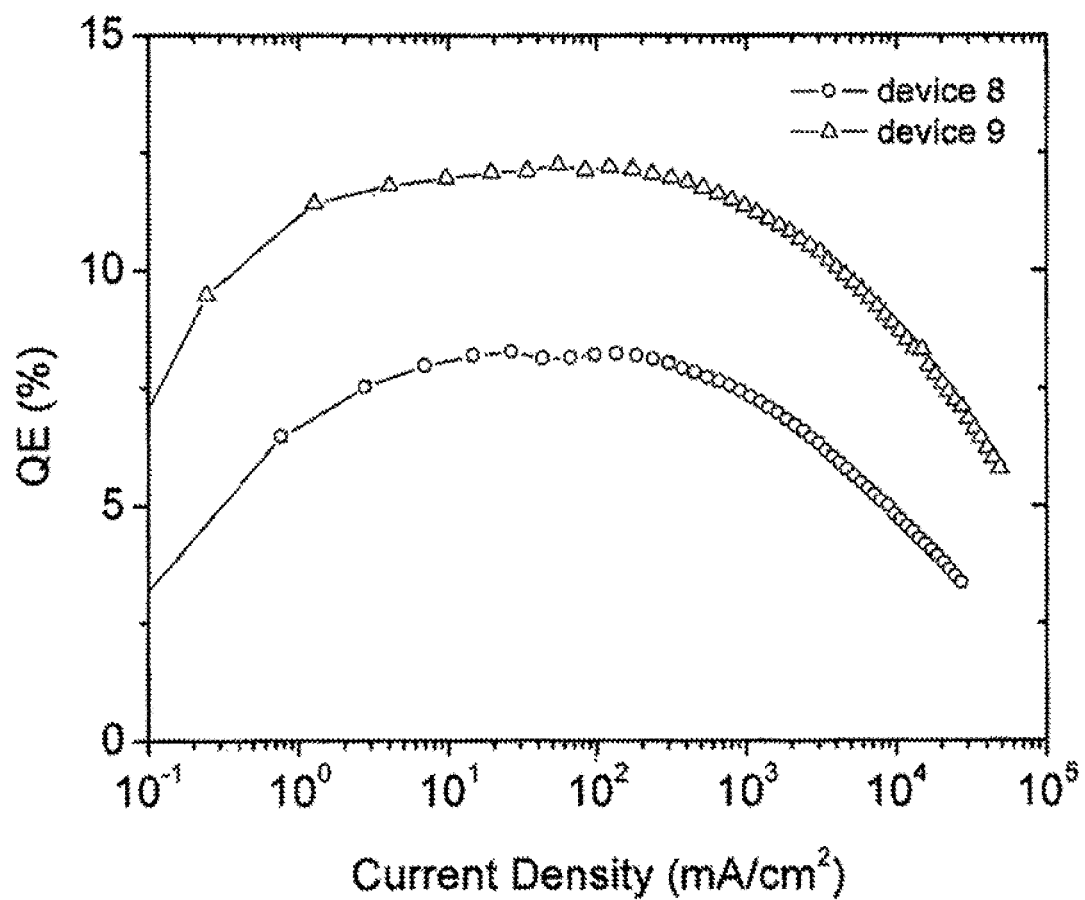
FIG. 7 shows quantum efficiency versus luminance for devices 8-9.

It is noted that substructures F-M are preferred. In these substructures, triphenylene is substituted with a phenyl ring that contains additional meta-aryl substitution which is an important difference when compared to an example that can be found in WO 2007/108362. It is important that the phenyl ring substituted on the triphenylene be further substituted in the meta position in order to limit direct phenyl-phenyl conjugation. It is believed that four para substituted phenyl rings may result in a low enough triplet energy to quench green phosphorescent emission. Therefore substructures F, G, H and I are the most preferred substructures where there are no more than three para substituted phenyl rings. The quenching effect of 4 para substituted phenyl rings is demonstrated by device data from comparative example 3. In this example, the two substituted phenyl rings and the fused rings of the triphenylene form a linear chain of 4 para substituted phenyl rings. The 77K PL for comparative example 3 gives a phosphorescent emission with a peak $\lambda_{max}$ of 493 nm. Devices using comparative example 3 result in very low quantum efficiency (FIG. 7) compared to the other examples.

Figure 5:
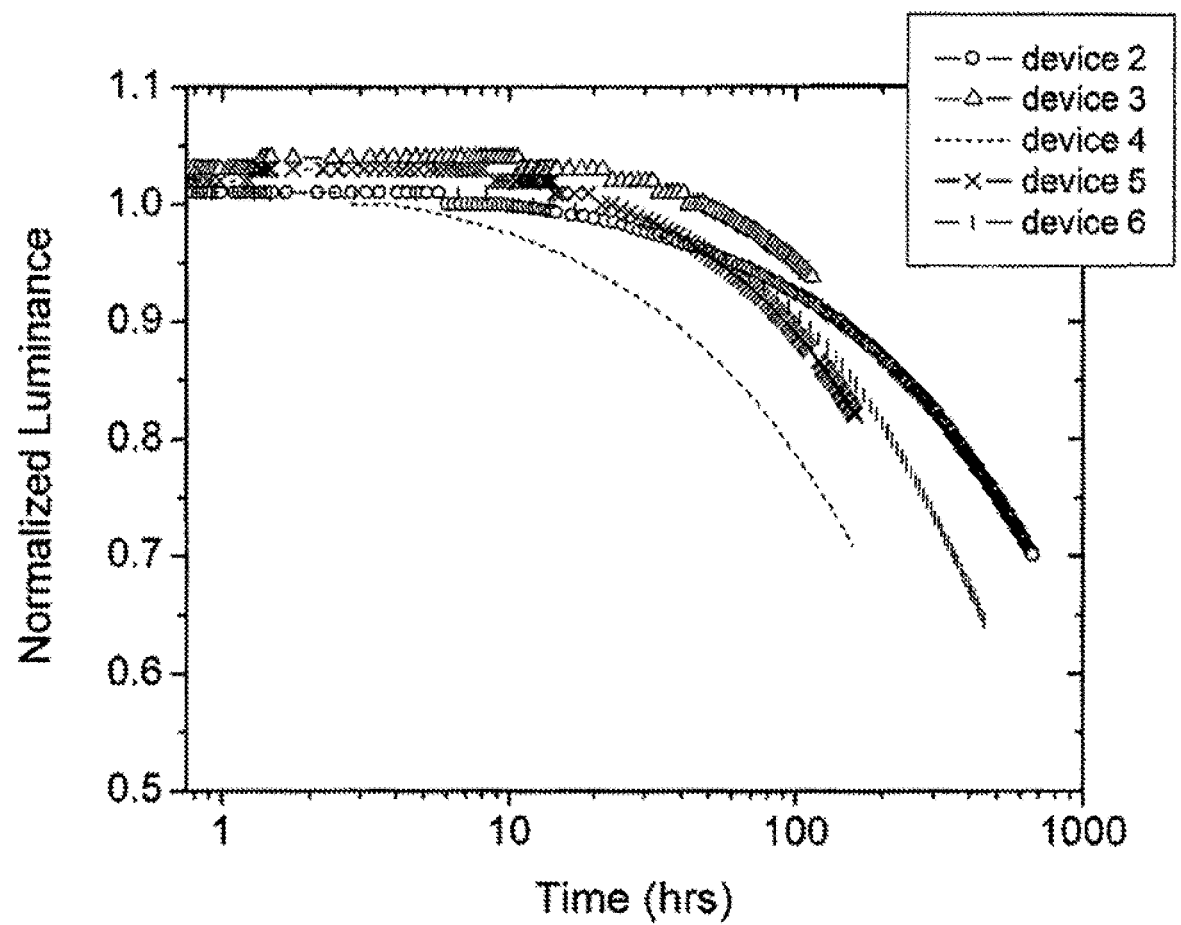
FIG. 5 shows lifetest data (40 mA/cm²) for devices 2-6.
Figure 8:
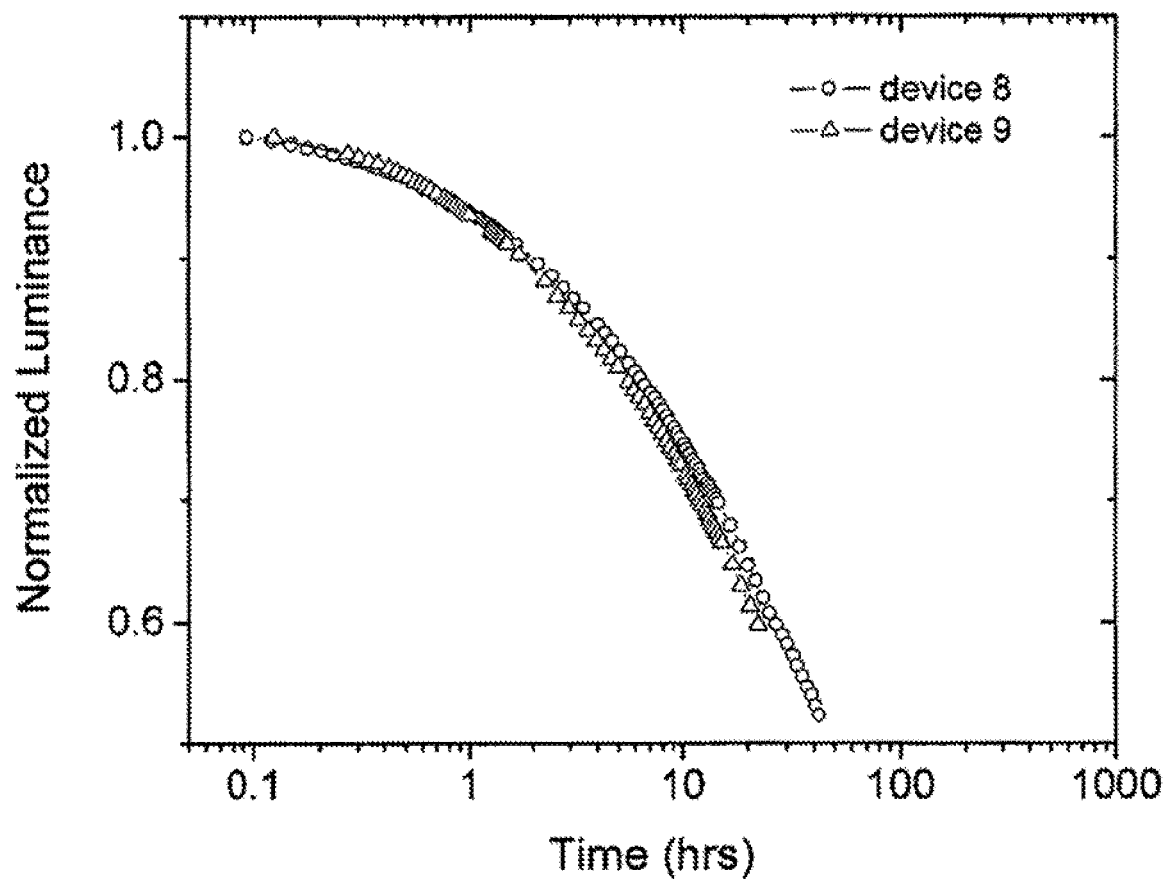
FIG. 8 shows lifetest data (40 mA/cm²) for devices 8-9.
Figure 9:
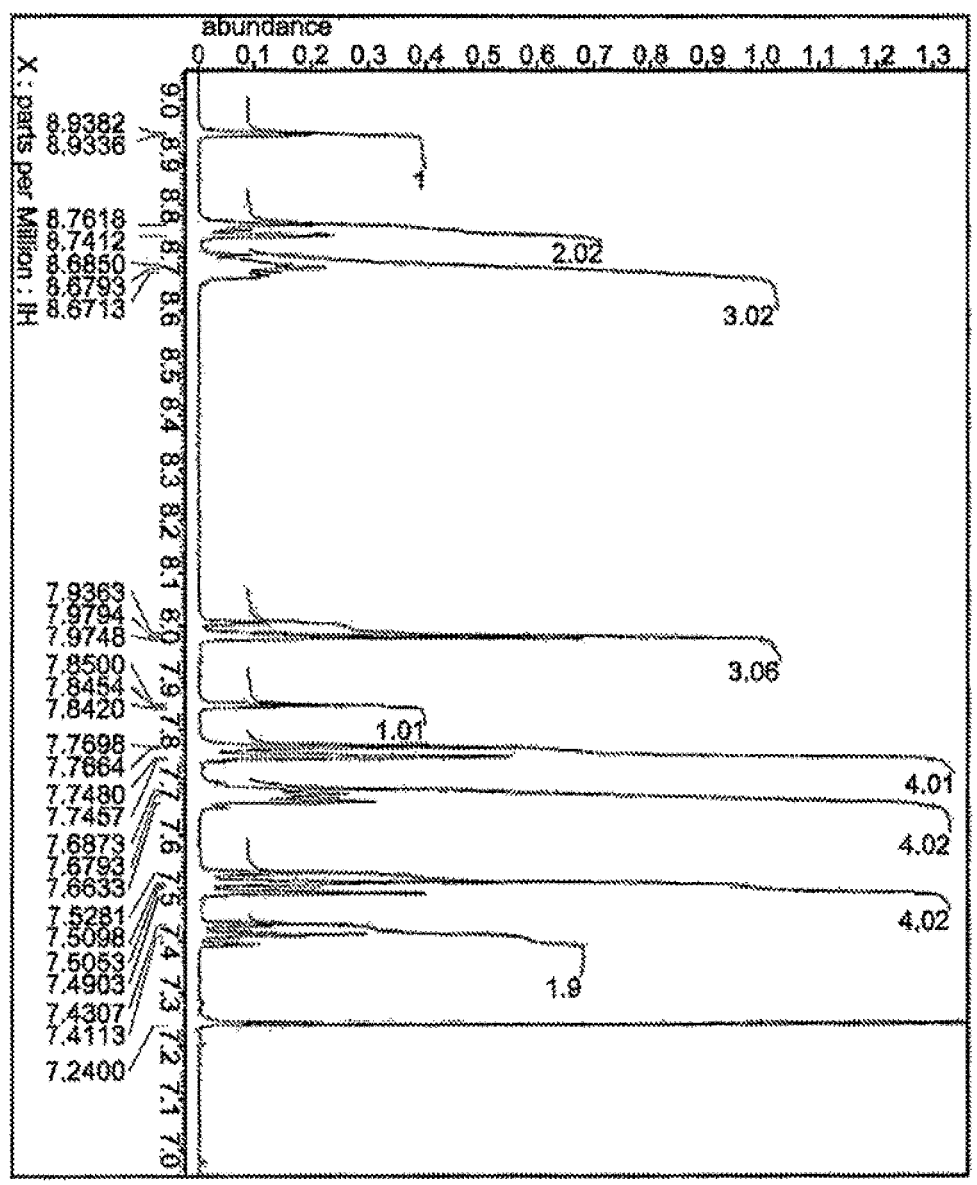
FIG. 9 shows the ¹H NMR spectra of compound 1.
Figure 10:
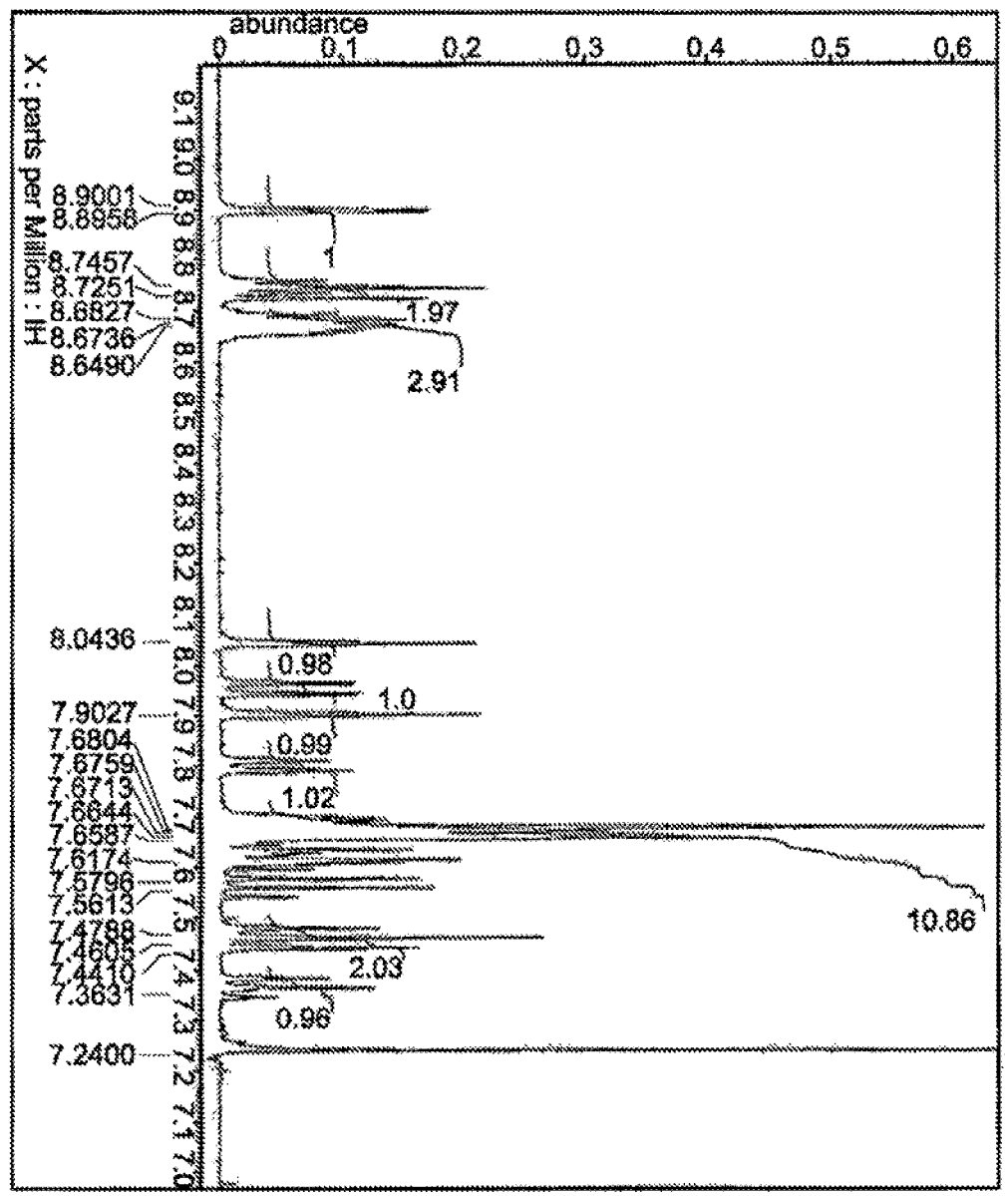
FIG. 10 shows the ¹H NMR spectra of compound 2.
Figure 11:
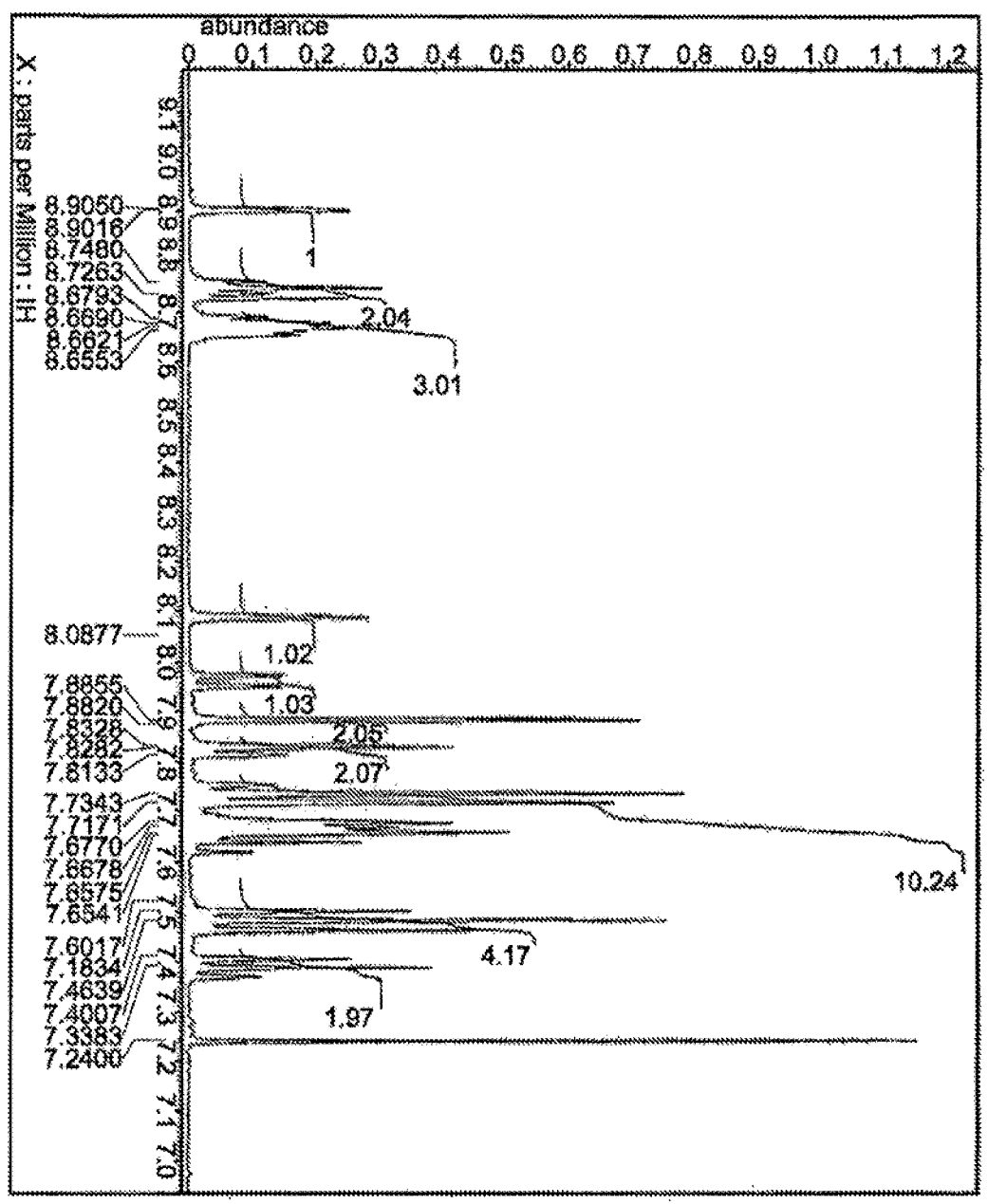
FIG. 11 shows the ¹H NMR spectra of compound 4.
Figure 12:
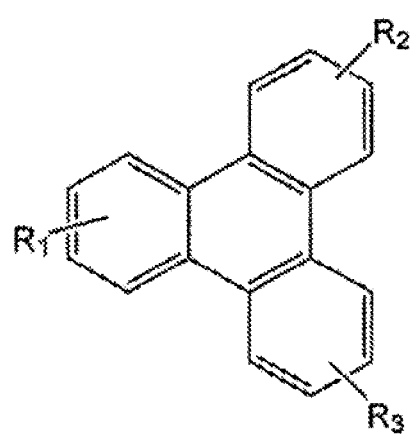
FIG. 12 shows a single triphenylene chromophore.

In addition it is preferred that there be additional meta-aryl substitutions in order to give the material a high enough molecular weight for sublimation and thin film thermal stability properties. If the molecular weight of the material is too low, the material will sublime at a very low temperature making the deposition process difficult to control. In addition, a very low molecular weight may result in a material that has a low glass transition temperature ($T_g$). If a material has a low $T_g$ and if it is very planar with high symmetry, the material may not form a stable amorphous film and may tend to crystallize. Low $T_g$ may result in poor thermal stability and can also result in poor device performance. Comparative examples 3 and 4 do not have additional phenyl substitutions and it is believed that their low molecular weight results in poor thermal stability and therefore poor device performance. This is shown by the device lifetime in FIG. 8. Devices 8 and 9 that use comparative example 3 and 4, respectively, have very short half lifetime ($T_{50}$) of <100 hrs when driven at a constant current density of 40 mA/cm$^2$ as shown in FIG. 8. Devices 2-6 use host materials with higher molecular weight and therefore result in much better device stability, as shown in FIG. 5 where $T_{50}$>>100 hrs.

The single triphenylene chromophore aspect of the invention describes single triphenylene containing materials for use as hosts and enhancement layers in phosphorescent organic light emitting diodes. These materials may offer advantages over hosts and enhancement layers containing two triphenylene chromophores. Single triphenylene containing derivatives may be easier to synthesize as only a single coupling reaction of triphenylene is required. In addition, these materials may be more soluble allowing for purification techniques, such as, column chromatography and recrystallization. The improved solubility can also allow for these materials to be used as materials in devices that are fabricated by a solvent process, such as spin casting or ink jet printing. Finally, it has been experimentally realized that single triphenylene hosts, did not red shift the emission of the phosphorescent dopant as compared to devices fabricated with the comparative examples 1 and 2. This effect may allow for devices to be fabricated that have improved color saturation.

Material Definitions:

As used herein, abbreviations refer to materials as follows:
CBP: 4,4'-N,N-dicarbazole-biphenyl
m-MTDATA 4,4',4"-tris(3-methylphenylphenlyamino)triphenylamine
$Alq_3$: 8-tris-hydroxyquinoline aluminum
Bphen: 4,7-diphenyl-1,10-phenanthroline
n-BPhen: n-doped BPhen (doped with lithium)
$F_4$-TCNQ: tetrafluoro-tetracyano-quinodimethane
p-MTDATA: p-doped m-MTDATA (doped with $F_4$-TCNQ)
$Ir(ppy)_3$: tris(2-phenylpyridine)-iridium
$Ir(ppz)_3$: tris(1-phenylpyrazoloto,N,C(2')iridium(III)
BCP: 2,9-dimethyl-4,7-diphenyl-1,10-phenanthroline
TAZ: 3-phenyl-4-(1'-naphthyl)-5-phenyl-1,2,4-triazole
CuPc: copper phthalocyanine.
ITO: indium tin oxide
NPD: N,N'-diphenyl-N—N'-di(1-naphthyl)-benzidine
TPD: N,N'-diphenyl-N—N'-di(3-toly)-benzidine
BAlq: aluminum(III)bis(2-methyl-8-hydroxyquinolinato)4-phenylphenolate
mCP: 1,3-N,N-dicarbazole-benzene
DCM: 4-(dicyanoethylene)-6-(4-dimethylaminostyryl-2-methyl)-4H-pyran
DMQA: N,N'-dimethylquinacridone
PEDOT:PSS: an aqueous dispersion of poly(3,4-ethylenedioxythiophene) with polystyrenesulfonate (PSS)
HPT: 2,3,6,7,10,11-hexaphenyltriphenylene
2,7-DCP 2,7-N,N-dicarbazolephenanthrene
3,3'-DC-o-TerP 3,3'-dicarbazole-o-terphenyl
4,4'-DC-o-TerP 4,4'-dicarbazole-o-terphenyl
2,6'-DCN 2,6-N,N-dicarbazolenaphthalene
$Ir(5-Phppy)_3$ tris[5'-phenyl(2-phenylpyridine)]iridium(III)
$Ir(3-Meppy)_3$: tris(3-methyl-2-phenylpyridine) iridium(III)
$Ir(1-piq)_3$: tris(1-phenylisoquinoline)iridium(III)
$Ir(3-Mepq)_2(acac)$: bis[3-methyl-2-phenylquinoline)]iridium(III) acetylacetonate
$Ir(5-Phppy)_3$: tris[5-phenyl(2-phenylpyridine)]iridium(III)
$Ir(pq)_2(acac)$: bis[2-phenylquinoline)]iridium(III) acetylacetonate
2,2-BT: 2,2-bistriphenylene
HPT: 2,3,6,7,10,11-hexaphenyltriphenylene
H1NT 2,3,6,7,10,11-hexa(1-naphthyl)triphenylene
H2BT 2,3,6,7,10,11-hexa(2-biphenyl)triphenylene Specific representative embodiments of the invention will now be described, including how such embodiments may be made. It is understood that the specific methods, materials, conditions, process parameters, apparatus and the like do not necessarily limit the scope of the invention.

EXPERIMENTAL

Synthesis of Single Triphenylene Compound 1

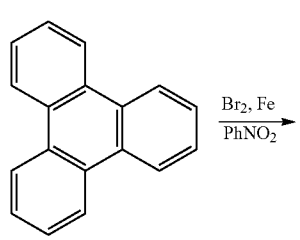

-continued

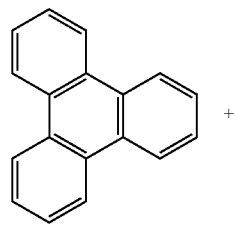

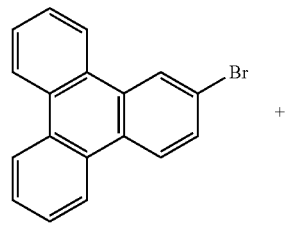

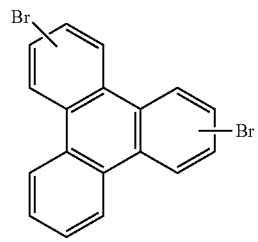

Triphenylene (19.0 g, 83 mmol) was added to and 600 mL of nitrobenzene. After all the triphenylene had dissolved, iron powder (0.07 g, 1.25 mmol) was added. The reaction flask was put in an ice bath. Bromine (20.0 g 125 mmol) in 50 mL of nitrobenzene was slowly added via addition funnel. After that, the reaction was stirred in an ice bath for 5 hours. HPLC was performed to monitor the reaction (TLC did not show separation of triphenylene and bromotriphenylenes). When the ratio of triphenylene:2-bromotriphenylene: dibromotriphenylenes reached approximately 2:7:1 (at 254 nm), the reaction was quenched by adding a $Na_2SO_3$ solution. The mixture was then extracted with $CH_2Cl_2$. The combined organic extract was dried over $MgSO_4$ and the $CH_2Cl_2$ was removed by rotovap. The remaining nitrobenzene was removed by vacuum distillation to yield the crude bromotriphenylene product which was used without further purification.

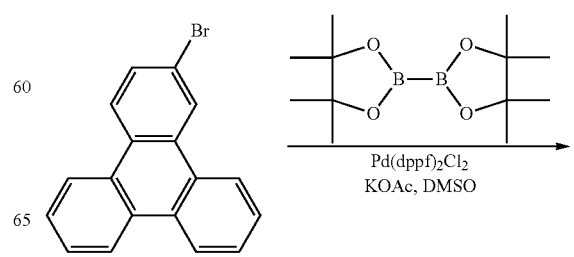

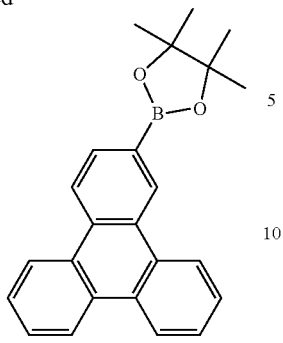

20.0 g of the bromotriphenylene mixture which contains about 70% of 2-bromotriphenylene based on HPLC monitored at 254 nm, 18.7 g (73 mmol) of bis(pinacolato)diboron, 1.6 g of Pd(dppf)$_2$Cl$_2$, 20 g (200 mmol) of potassium acetate, and 400 Ml of DMSO was mixed at room temperature under N$_2$. The mixture was degassed then heated up to 80° C. for 12 hours. After cooling to room temperature, the mixture was poured into ice water. The precipitate was then collected by filtration. The solid was dissolved in dichloromethane and dried over magnesium sulfate. The crude product was purified by column using a mixture of hexanes and dichloromethane (from 6:1 to 3:1) as eluent. 10 g of the pure product, 4,4,5,5-tetramethyl-2-(triphenylen-2-yl)-1,3,2-dioxaborolane, was isolated.

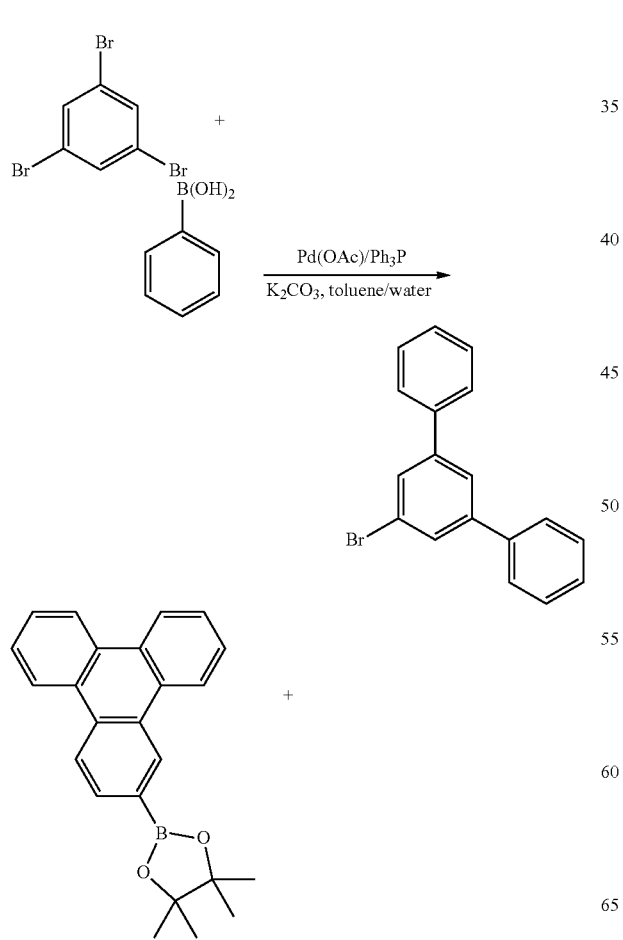

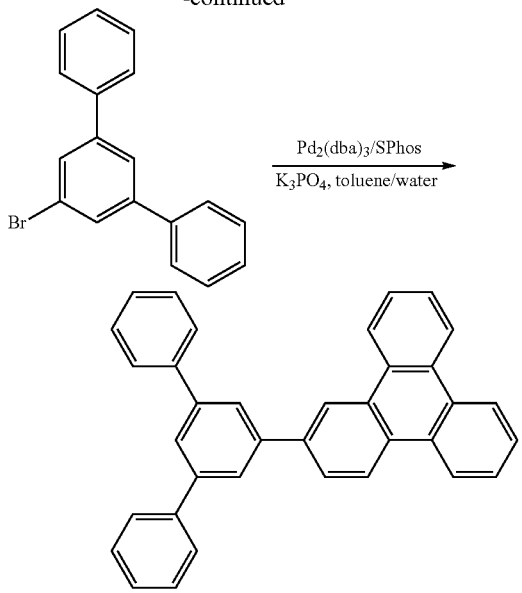

Compound 1

Synthesis of Single Triphenylene Compound 2

12 g (39 mmol) bromotriphenylene mixture containing a 2:7:1 mixture of unreacted triphenylene, monobromo and dibromo triphenylene, 13 g (86 mmol) 3-phenylboronic acid, 0.6 g (1.56 mmol) 2-dicyclohexylphosphino-2',6'-dimethoxybiphenyl (SPhos) and 25 g (117 mmol) potassium phosphate tribasic (K$_3$PO$_4$) are weighed in a round bottom flask. 150 mL toluene and 80 mL water were added to the flask as solvent. The solution was purged with nitrogen and 0.4 g (0.39 mmol) of tris(dibenzylideneacetone)dipalladium(0) [Pd$_2$(dba)$_3$] was added. The solution was heated to reflux for twelve hours. Upon cooling, the organic layer was separated, and dried with MgSO$_4$. The product was readily separated by column chromatography from triphenylene and di-(3-methoxyphenyl) substituted triphenylene using Hexane/dichloromethane as eluent (1/0 gradient to 3/2). The solvent was removed by rotary evaporation, and the product, 2-(3-methoxyphenyl)triphenylene, was dried overnight under vacuum.

separation of 4,4,5,5-tetramethyl-2-(triphenylen-2-yl)-1,3,2-dioxaborolane from the corresponding disubstituted material is much more difficult and time consuming. Therefore the synthetic route for 3-(triphenylen-2-yl)phenyl trifluoromethanesulfonate is advantageous for obtaining high purity triphenylene based optoelectronic materials.

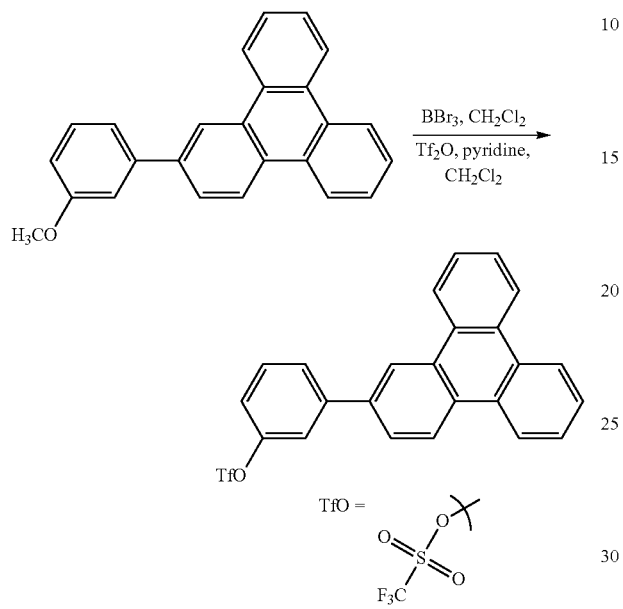

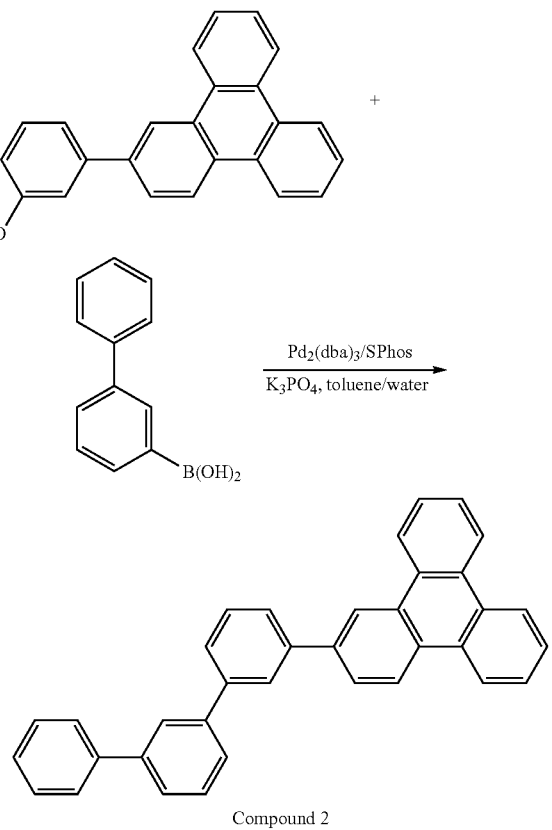

Compound 2

In a round bottom flask under nitrogen, 1.8 g (5.4 mmol) 2-(3-methoxyphenyl)triphenylene was dissolved in 25 mL anhydrous dichloromethane. The solution was cooled to −78° C. and 4 g (1.5 mL, 16 mmol) boron tribromide was added slowly via syringe. The solution was warmed to room temperature and stirred overnight. Ice was carefully added to quench unreacted BBr$_3$. The 3-(triphenylen-2-yl)phenol intermediate precipitated upon addition of ice, and dichloromethane was added to dissolve. The organic layer was separated and dried with MgSO$_4$, the dichloromethane was removed by rotary evaporation and the product was dried under vacuum.

1.7 g (5.3 mmol) of 3-(triphenylen-2-yl)phenol was added to a flask under nitrogen with 0.84 g (10.5 mmol) anhydrous pyridine and 100 mL anhydrous dichloromethane. The solution was cooled in an ice bath and 2.97 g (10.5 mmol) trifluoromethanesulfonic anhydride (Tf$_2$O) was added slowly via syringe. The solution was warmed to room temperature and stirred overnight. The solution was washed with water, dried with MgSO$_4$ and the solvent was removed by rotary evaporation. The product, 3-(triphenylen-2-yl)phenyl trifluoromethanesulfonate, was purified by column chromatography using hexane/dichloromethane as eluent (1/0 to 1/1 gradient)

It is noted here that the synthetic procedure for the functionalized intermediate, 3-(triphenylen-2-yl)phenyl trifluoromethanesulfonate has significant advantages over the previously described functional intermediate, 4,4,5,5-tetramethyl-2-(triphenylen-2-yl)-1,3,2-dioxaborolane. Due to significant differences in polarity and excellent solubility, 2-(3-methoxyphenyl)triphenylene can be readily purified by column chromatography from the mixture of unreacted triphenylene and the disubstituted 3-methoxyphenyl triphenylene. In comparison, it is found in practice that the Synthesis of Single Triphenylene Compound 3

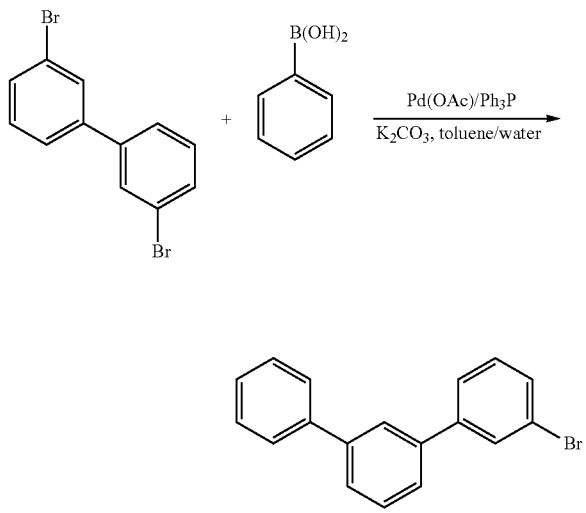

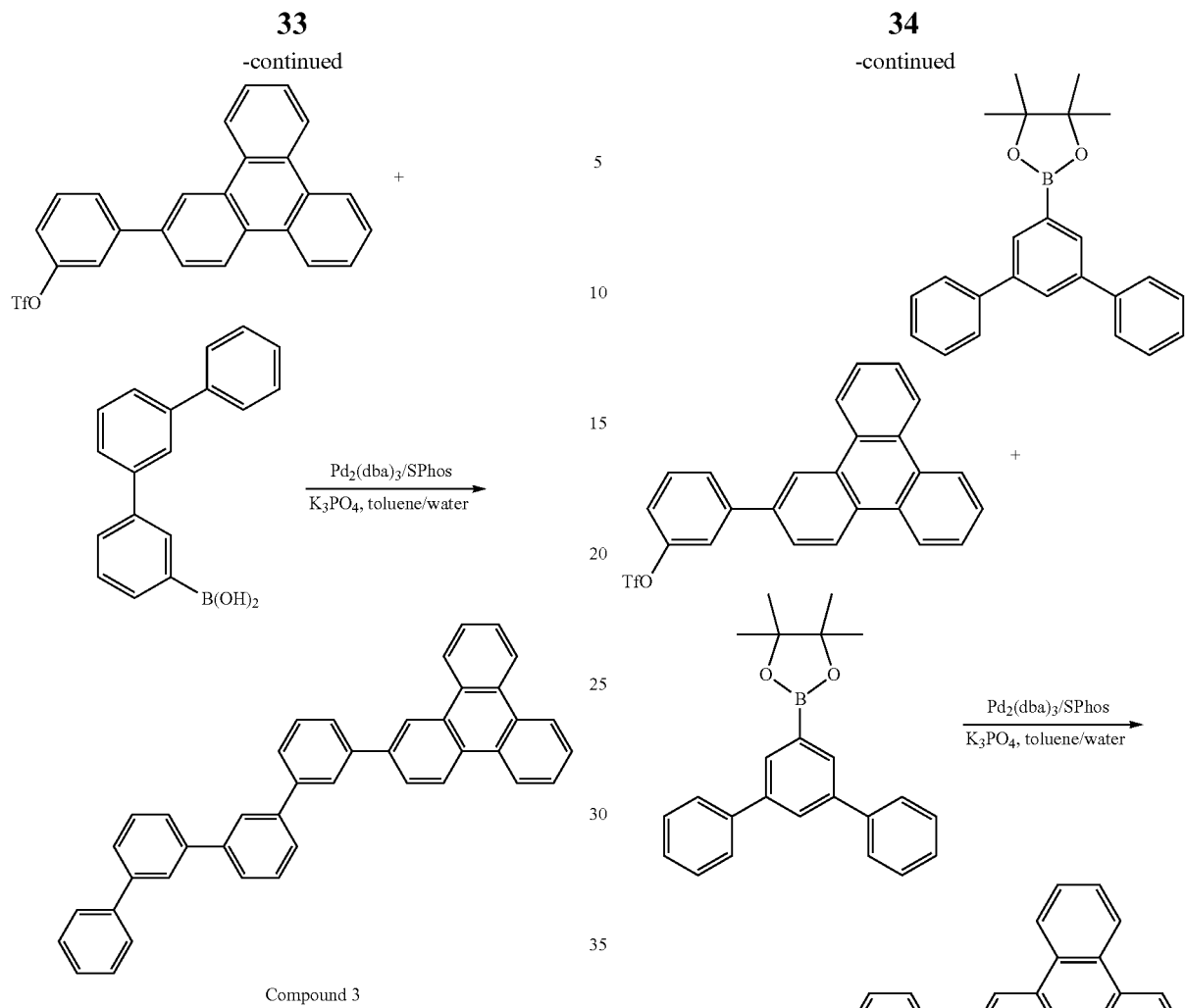
Compound 3
Synthesis of Single Triphenylene Compound 4
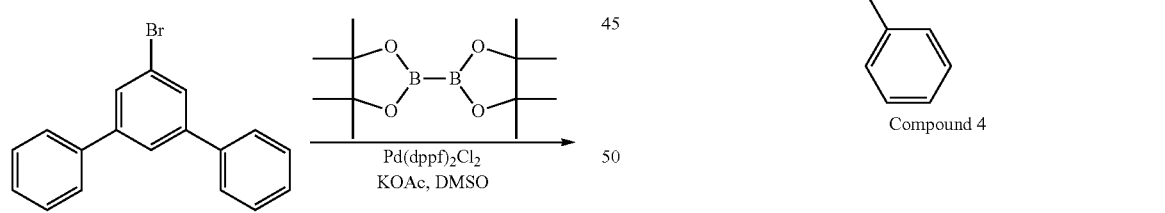
Compound 4
Synthesis of Single Triphenylene Compound 5
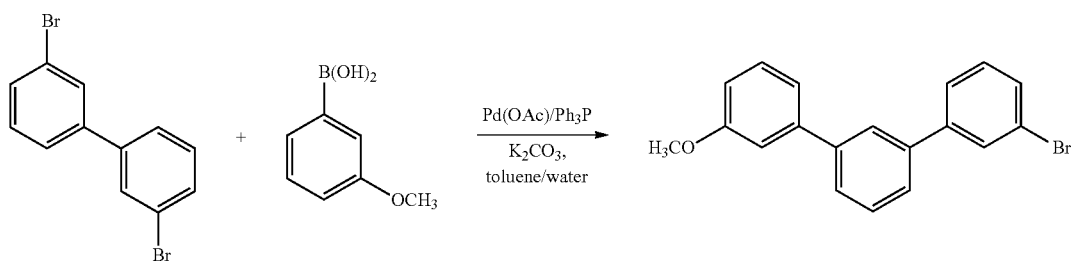

-continued
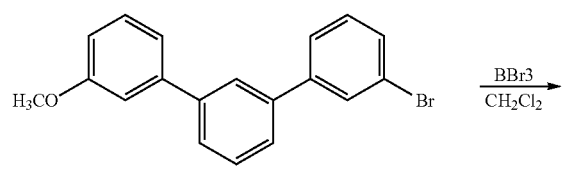
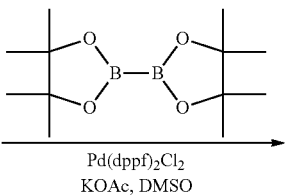
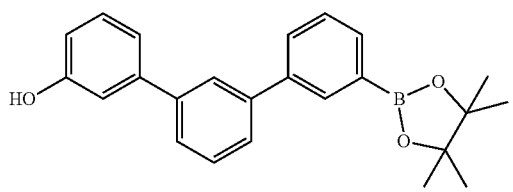
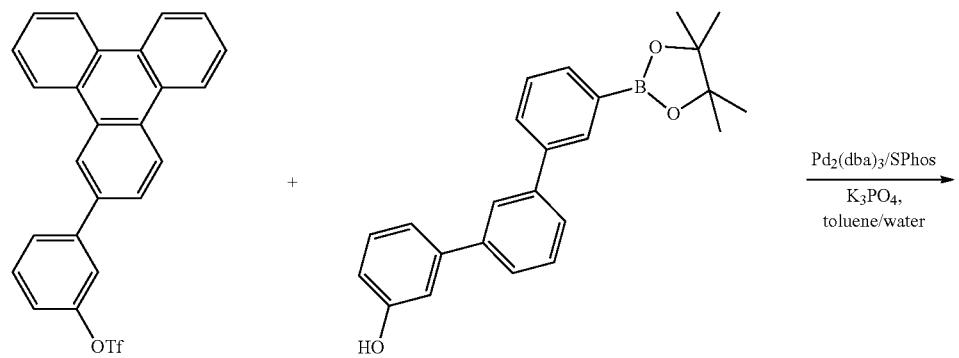
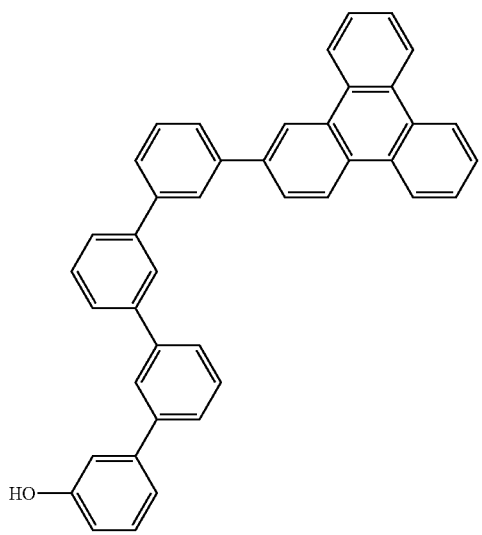

37
-continued
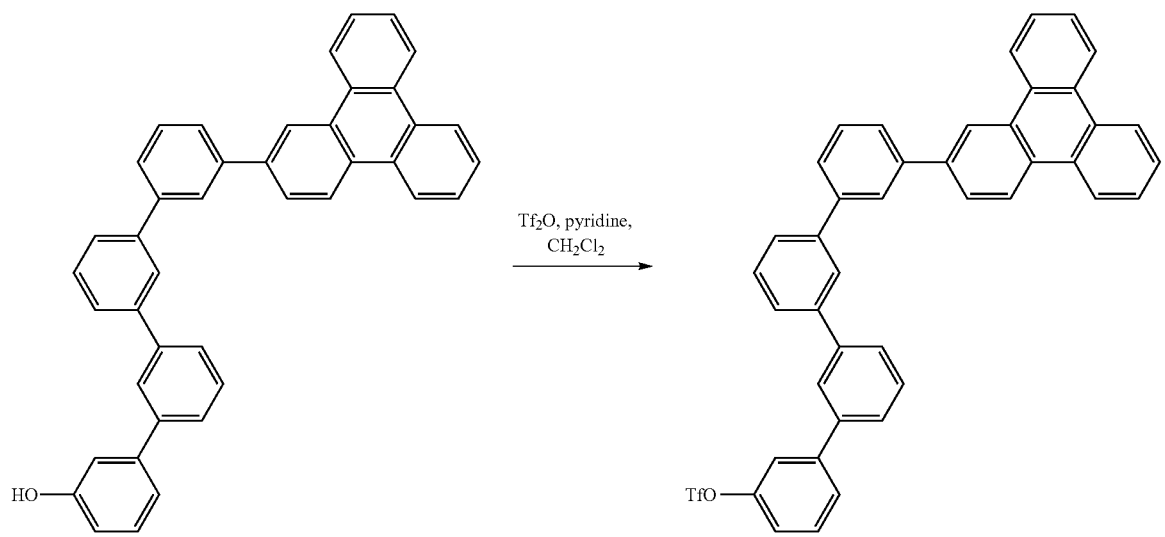
38
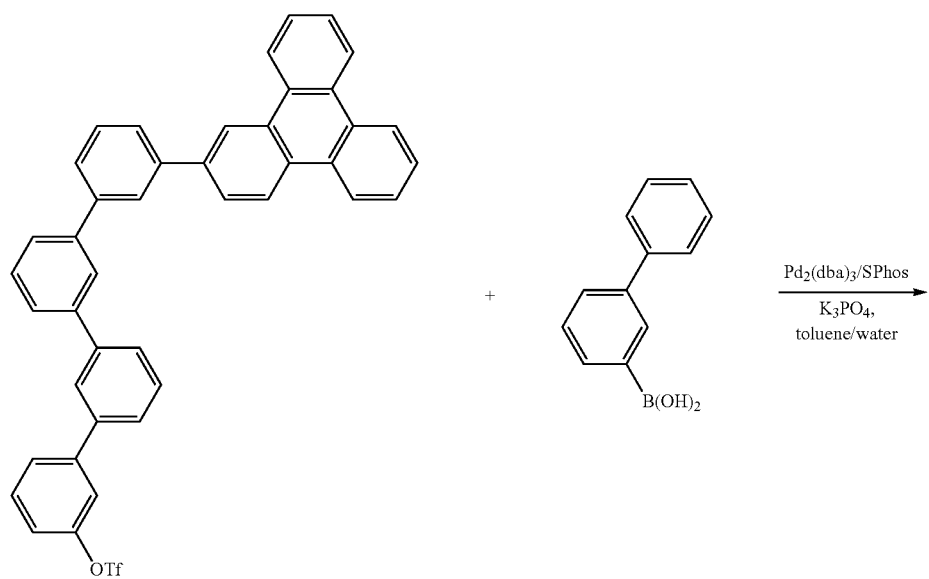

-continued
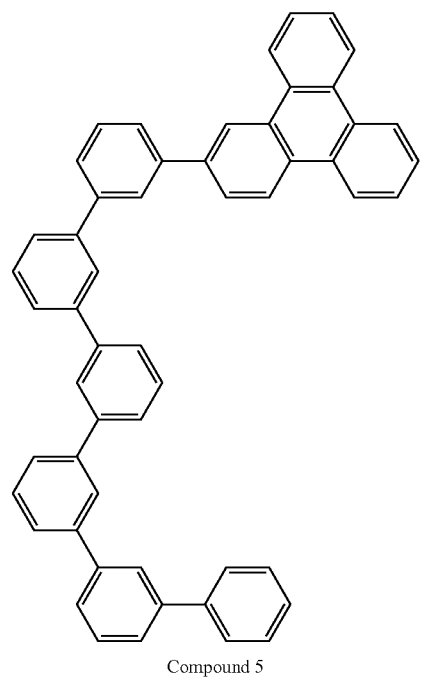
Compound 5
Synthesis of Single Triphenylene Compound 6
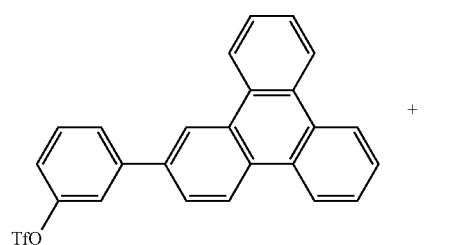
-continued
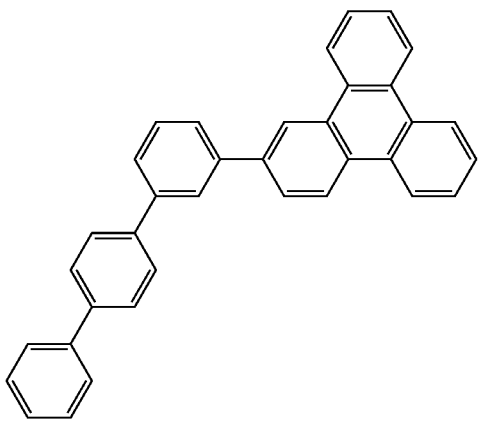
Compound 6
Synthesis of Single Triphenylene Compound 7
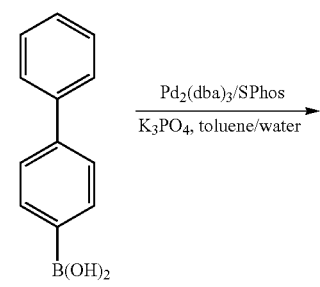
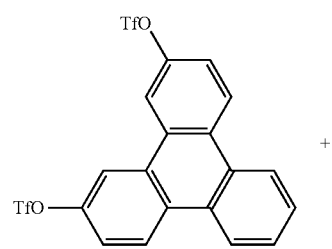

-continued

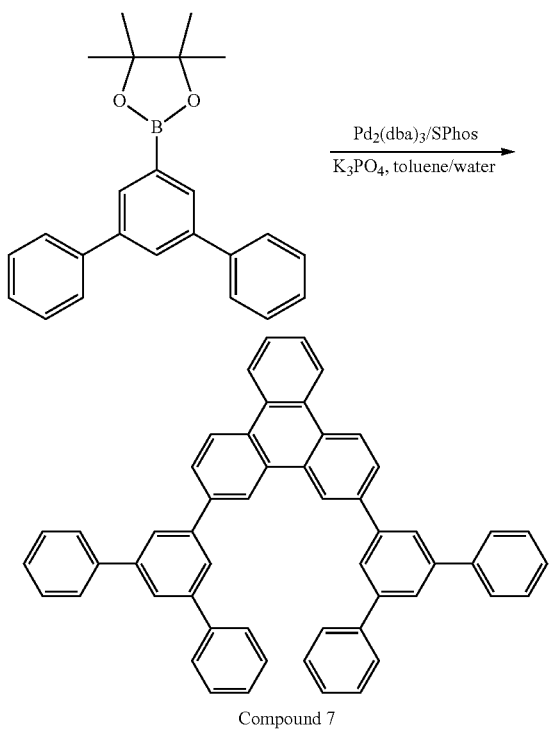

Compound 7

Synthesis of Single Triphenylene Compound 8

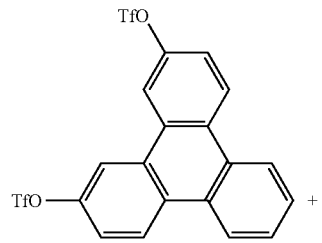

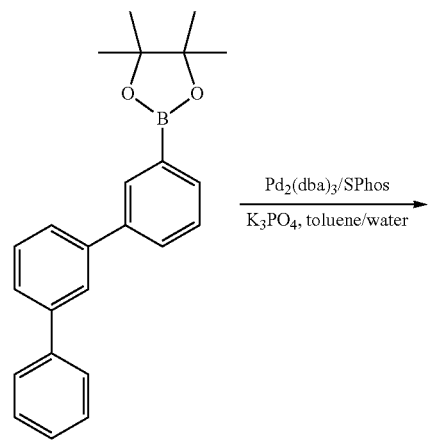

-continued

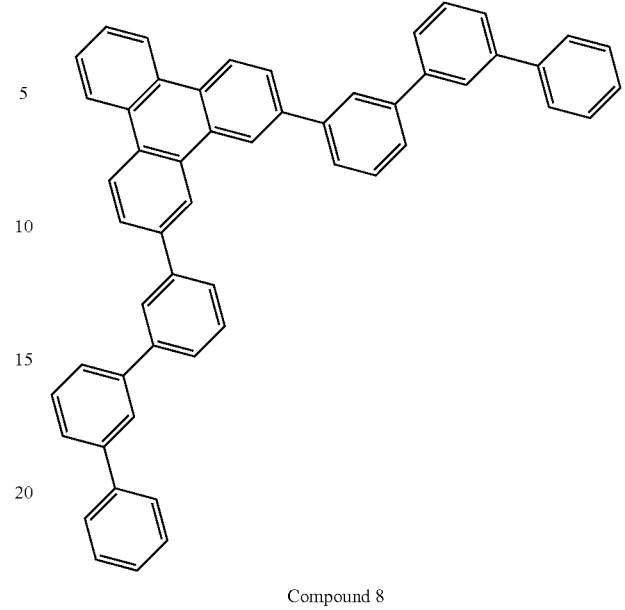

Compound 8

Synthesis of Single Triphenylene Compound 9

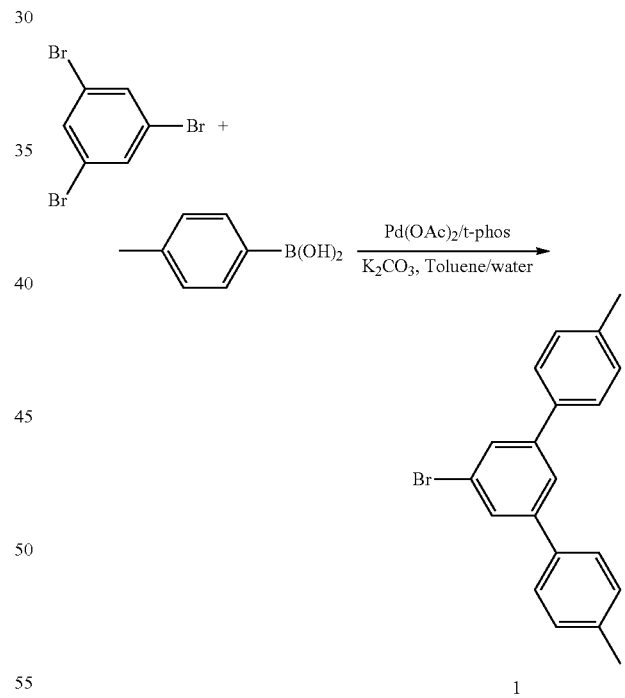

A mixture of tribromobenzene (10 g, 31.8 mmol), p-tolyl-boronic acid (7.3 g, 54.0 mmol), triphenylphosphine (1.7 g, 6.4 mmol) and potassium carbonate (23.7 g, 172 mmol) in 150 mL toluene and 50 mL water was prepared. Nitrogen was bubbled directly in the mixture for 20 minutes. Then palladium acetate was added (0.36 g, 1.6 mmol). Nitrogen was bubbled again in the mixture for another 10 minutes. The mixture was heated to reflux under nitrogen overnight. The reaction mixture was cooled to RT. The organic layer was separated and the aqueous layer was extracted with dichloromethane. The combined organic layers were dried over magnesium sulfate, filtered and evaporated. The mixture was purified by silica column with pure hexanes to gain 5.0 gram white powder (47%).

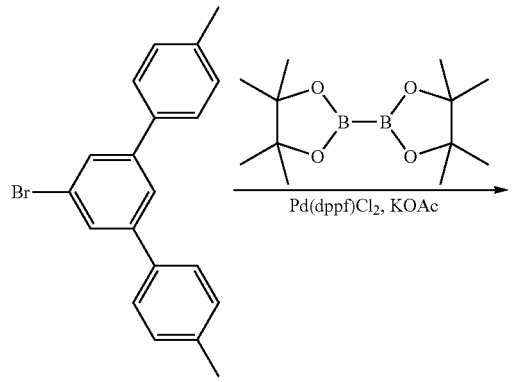

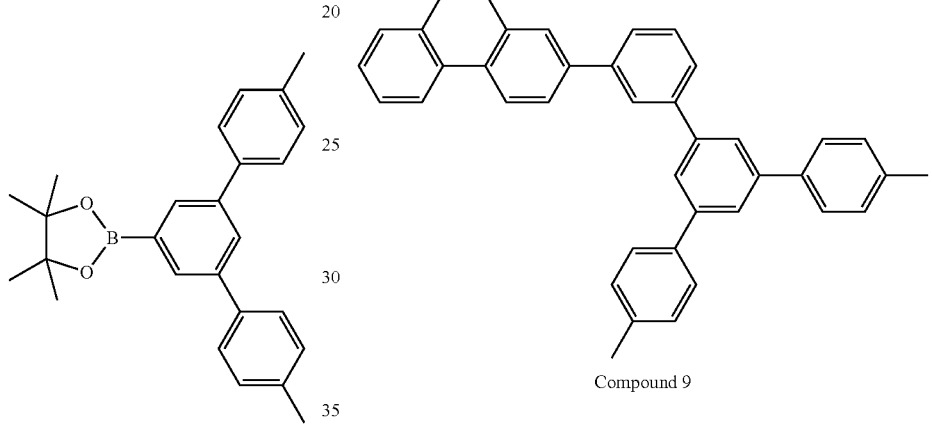

Compound 9

A mixture of 5'-bromo-4,4''-dimethyl-m-terphenyl (1) (4.5 g, 13.3 mmol), pinacol diborate (4.1 g, 16.0 mmol), potassium acetate (3.9 g, 40 mmol) in 100 mL of anhydrous dioxane was prepared. Nitrogen was bubbled directly in the mixture for 15 minutes. Next [1,1'-Bis(diphenylphosphino)ferrocene]dichloropalladium(II) (0.33 g, 0.4 mmol) was added and then the nitrogen was bubbled in the mixture for another 10 minutes. The reaction mixture was heated to 80° C. overnight under nitrogen. The next day the reaction mixture was cooled and diluted with dichloromethane and washed with water twice. The organic layer was dried over magnesium sulfate, filtered and evaporated. The mixture was purified by column chromatography eluting with up to 5% ethyl acetate/hexanes. The solid was further purified by the recrystallization from hot hexanes to get 3.9 gram white solid (76%).

A mixture of intermediate 2 (3.5 g, 9.1 mmol) and triphenylene triflate (3.75 g, 8.3 mmol), potassium phosphate tribasic (5.3 g, 24.9 mmol) in 120 mL toluene and 40 mL water was prepared. Nitrogen was bubbled directly in the mixture for 15 minutes. Next tris(dibenzylideneacetone)dipalladium (0.76 mg, 0.08 mmol) and SPhos (136 mg, 0.33 mmol) was added, and then nitrogen was bubbled in the mixture for another 10 minutes. The reaction mixture was refluxed overnight under nitrogen. The next day the reaction mixture was cooled to room temperature. The organic layer was separated and the aqueous layer was extracted by dichloromethane. The combined organic layers were dried over magnesium sulfate, filtered and concentrated under reduced pressure. The mixture was purified by column chromatography eluting with up to 30% 30% dichloromethane/hexanes to gain 4.7 gram white powder (92%).

Synthesis of Single Triphenylene Compound 10

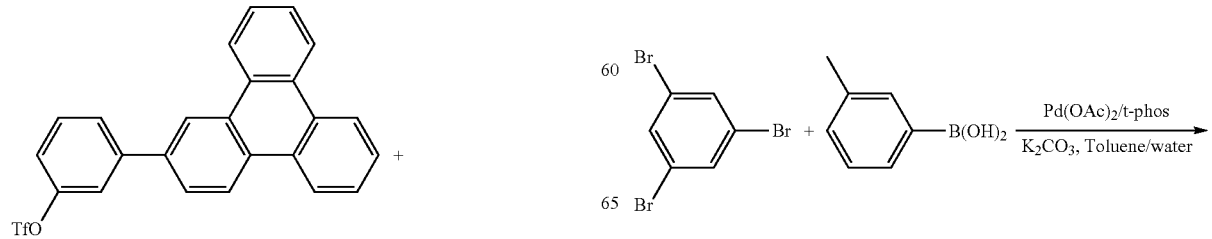

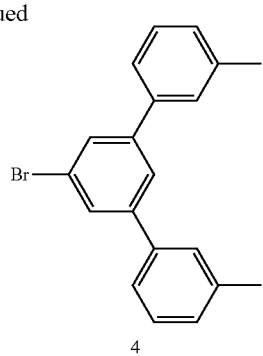

4

A mixture of tribromobenzene (10 g, 31.8 mmol), p-tolylboronic acid (7.3 g, 54.0 mmol), triphenylphosphine (1.7 g, 6.4 mmol) and potassium carbonate (23.7 g, 172 mmol) in 150 mL toluene and 50 mL water was prepared. Nitrogen was bubbled directly in the mixture for 20 minutes. Then palladium acetate was added (0.36 g, 1.6 mmol). Nitrogen was bubbled again in the mixture for another 10 minutes. The mixture was heated to reflux under nitrogen overnight. The reaction mixture was cooled to room temperature. The organic layer was separated and the aqueous layer was extracted with dichloromethane. The combined organic layers were dried over magnesium sulfate, filtered and evaporated. The mixture was purified by silica column with pure hexanes to gain 3.4 gram colorless oil (32%).

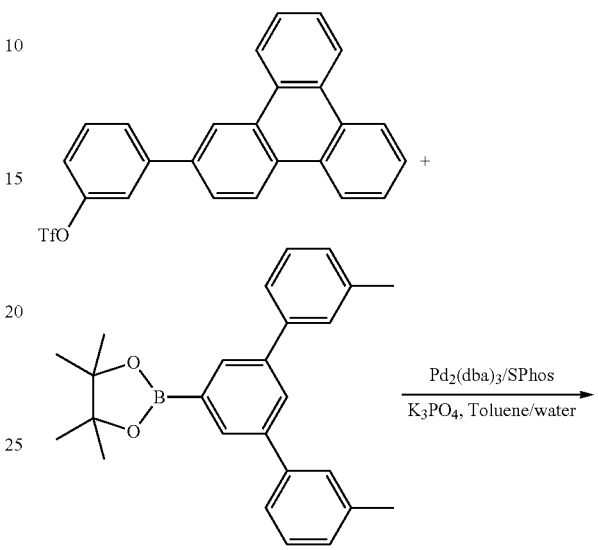

5

A mixture of 5'-bromo-4,4''-dimethyl-m-terphenyl (4) (3.5 g, 10 mmol), pinacol diborate (3.2 g, 12 mmol), potassium acetate (3.1 g, 31 mmol) in 100 mL of anhydrous dioxane was prepared. Nitrogen was bubbled directly in the mixture for 15 minutes. Next was added [1,1'-Bis(diphenylphosphino)ferrocene]dichloropalladium(II) (0.25 g, 0.31 mmol) and then the nitrogen was bubbled in the mixture for another 10 minutes. The reaction mixture was heated to 80° C. overnight under nitrogen. The next day the reaction mixture was cooled and diluted with dichloromethane and washed with water twice. The organic layer was dried over magnesium sulfate, filtered and evaporated. The mixture was purified by column chromatography eluting with up to 5% ethyl acetate/hexanes. The solid was further purified by recrystallization from hot hexanes to get 2.5 gram white solid (63%).

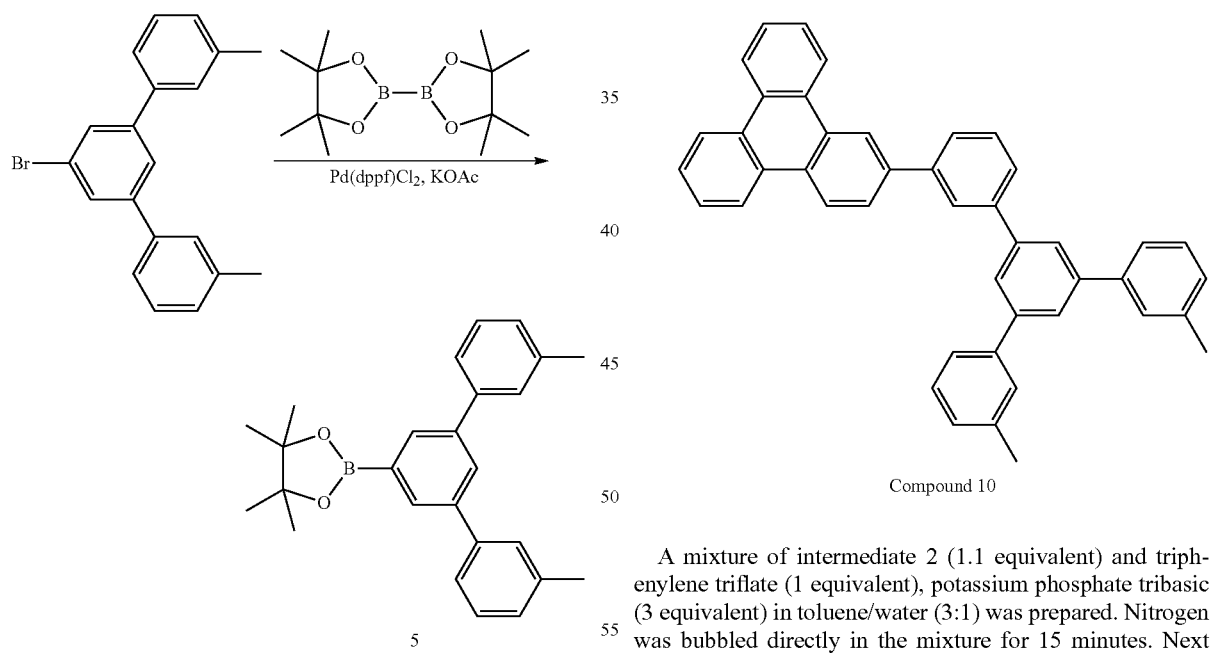

Compound 10

A mixture of intermediate 2 (1.1 equivalent) and triphenylene triflate (1 equivalent), potassium phosphate tribasic (3 equivalent) in toluene/water (3:1) was prepared. Nitrogen was bubbled directly in the mixture for 15 minutes. Next tris(dibenzylideneacetone)dipalladium (1% equivalent) and SPhos (0.04 equivalent) were added, and then nitrogen was bubbled in the mixture for another 10 minutes. The reaction mixture was refluxed overnight under nitrogen. The next day the reaction mixture was cooled to room temperature. The organic layer was separated and the aqueous layer was extracted by dichloromethane. The combined organic layers were dried over magnesium sulfate, filtered and concentrated under reduced pressure. The mixture was purified by column chromatography eluting with up to 30% dichloromethane/hexanes to gain the final product.

Synthesis of Single Triphenylene Compound 11

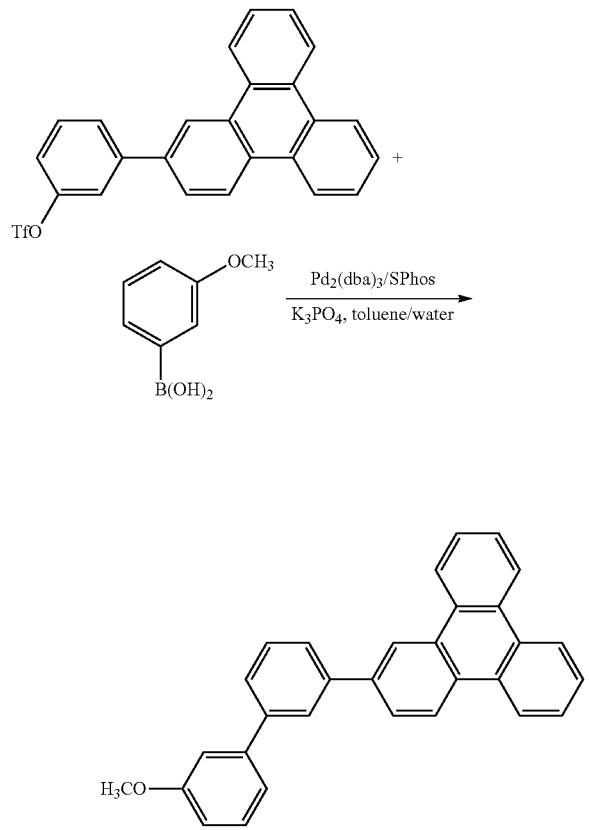

12.9 g (28.5 mmol) 3-(triphenylen-2-yl)phenyl trifluoromethanesulfonate, 6.5 g (42.8 mmol) 3-phenylboronic acid, 0.47 g (1.1 mmol) 2-dicyclohexylphosphino-2',6'-dimethoxybiphenyl (SPhos) and 18.2 g (85.5 mmol) potassium phosphate tribasic (K$_3$PO$_4$) were weighed in a round bottom flask. 150 mL toluene and 80 mL water were added to the flask as solvent. The solution was purged with nitrogen and 0.26 g (0.28 mmol) of tris(dibenzylideneacetone)dipalladium (0) [Pd$_2$(dba)$_3$] was added. The solution was heated to reflux for twelve hours. Upon cooling, the organic layer was separated, and dried with MgSO$_4$.

The product was readily separated by column chromatography using hexane/dichloromethane as eluent (1/0 gradient to 3/2). The solvent was removed by rotary evaporation resulting in 11.7 g (28 mmol) of the product, 2-(3'-methoxybiphenyl-3-yl)triphenylene,

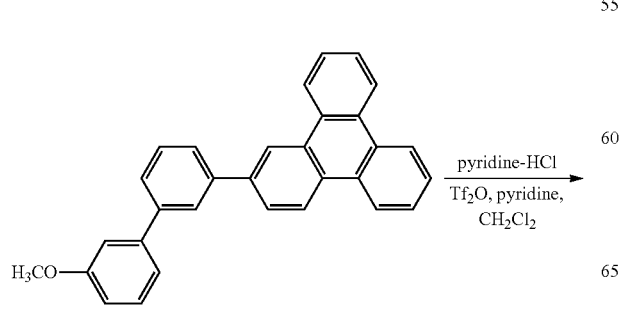

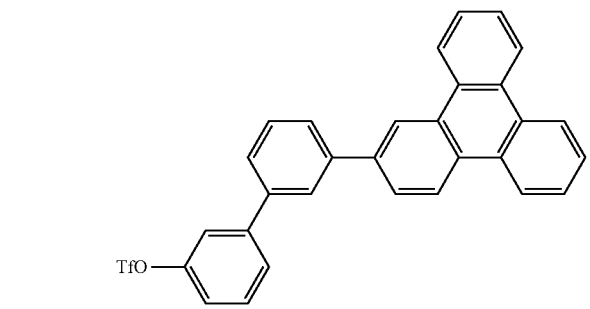

In a round bottom flask under nitrogen, 11.5 g (28 mmol) 2-(3'-methoxybiphenyl-3-yl)triphenylene and 21.1 g (183 mmol) pyridine hydrochloride were heated to 204° C. Upon cooling, water was added and extracted with dichloromethane. The combined organic fractions were washed with additional water and the solvent was removed by rotary evaporation. The solid was drypacked on celite and the product purified by column chromatography using hexanes:dicholormethane (1:4) as eluent. The solvent was removed by rotary evaporation resulting in 8.6 g (22 mmol) of the product, 3'-(triphenylen-2-yl)biphenyl-3-ol.

8.6 g (22 mmol) of 3'-(triphenylen-2-yl)biphenyl-3-ol was added to a flask under nitrogen with 3.4 g (43.4 mmol) anhydrous pyridine and 450 mL anhydrous dichloromethane. The solution was cooled in an ice bath and 12.2 g (43.4 mmol) trifluoromethanesulfonic anhydride (Tf$_2$O) was added slowly via syringe. The solution was warmed to room temperature and stirred overnight. The solution was washed with water, dried with MgSO$_4$ and solvent was removed by rotary evaporation. The product, 3'-(triphenylen-2-yl)biphenyl-3-yl trifluoromethanesulfonate, was purified by column chromatography using hexane/dichloromethane as eluent (1/0 to 1/1 gradient) resulting in 10.7 g (20.2 mmol).

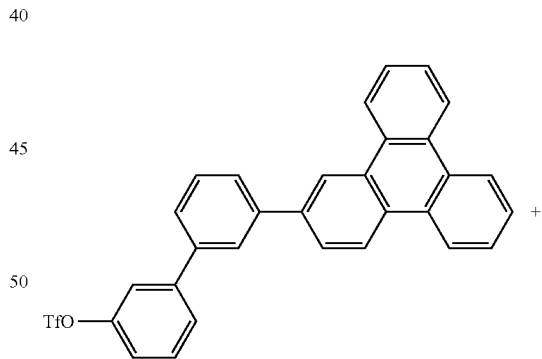

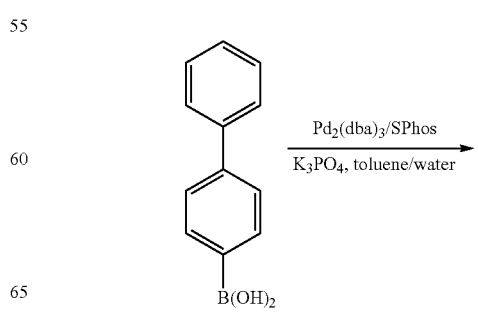

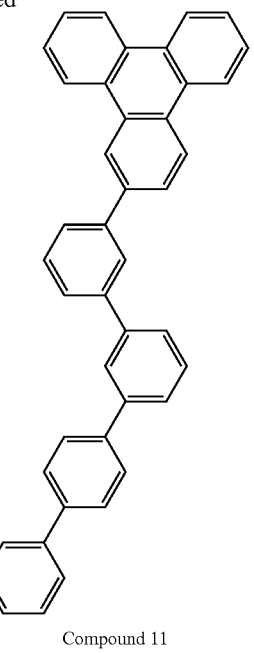

Compound 11

9.7 g (18.4 mmol) 3'-(triphenylen-2-yl)biphenyl-3-yl trifluoromethanesulfonate, 5.5 g (27.7 mmol) 4-biphenylboronic acid, 0.3 g (0.74 mmol) 2-dicyclohexylphosphino-2',6'-dimethoxybiphenyl (SPhos) and 11.7 g (55.3 mmol) potassium phosphate tribasic ($K_3PO_4$) were weighed in a round bottom flask. 150 mL toluene and 80 mL water were added to the flask as solvent. The solution was purged with nitrogen and 0.17 g (0.18 mmol) of tris(dibenzylideneacetone)dipalladium (0) [$Pd_2(dba)_3$] was added. The solution was heated to reflux for twelve hours. Upon cooling, the organic layer was separated, and dried with $MgSO_4$ and filtered. The solvent was removed by rotary evaporation and the solid was recrystallized in toluene and sublimed under high vacuum resulting in 6 g (11.2 mmol) of compound 11.

Synthesis of Single Triphenylene Compound 12

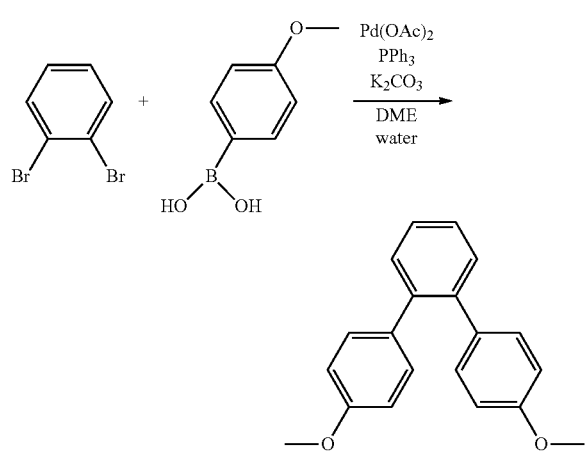

4,4'-Dimethoxy-o-terphenyl

A mixture was prepared consisting of 1,2-dibromobenzene (50 g, 212 mmol), 4-methoxyphenylboronic acid (78 g, 513 mmol), triphenylphosphine (11.12 g, 42.2 mmol), potassium carbonate (73.25 g, 530 mmol), dimethoxyethane (290 mL), and water (290 mL). Nitrogen was bubbled directly into the mixture for 20 minutes. Palladium acetate was added (4.76 g, 21.2 mmol) and the mixture was heated to reflux overnight under nitrogen. The reaction mixture was cooled and water and dichloromethane was added. The layers were separated and the aqueous layer was extracted with dichloromethane. The combined organic layers were filtered through Celite and washed with brine, dried over magnesium sulfate, filtered, evaporated to a yield a black oil. The crude material was purified by column chromatography eluting with 0 to 100% dichloromethane/hexanes. The cleanest fractions were purified by distillation using a Kugelrohr at 200 to 220° C. The product remained in the boiling flask and the impurity distilled into the bulb along with some product. Obtained 49 g (80%) of clean product.

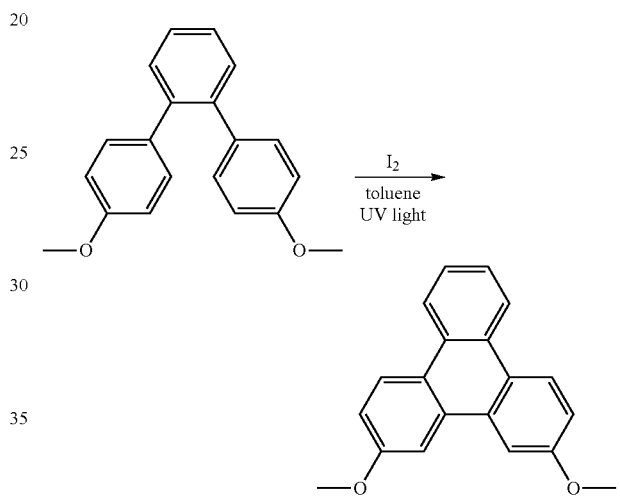

2,11-Dimethoxytriphenylene 12.4 g (42.7 mmol) of 4,4'dimethoxy-o-terphenyl and 16 g (63.0 mmol) iodine chips was placed in a 250 mL reaction vessel. 200 mL of toluene was added followed by 30 mL of propylene oxide. The photoreactor was set up with a condenser cooled by a recirculating chiller. A 400 W medium pressure mercury lamp was used as the light source. The reaction vessel was placed in a cabinet. The lamp was ignited (the chiller temperature was set such that the water exiting the reactor was maintained at between 20° C. and 25° C. (monitored by a thermocouple attached the exit stream). The reaction was left on for 18 hours. A solid was filtered off and washed with hexanes, only recovered 2.2 g of material. The filtrate was diluted with toluene and washed with sodium sulfate solution. The aqueous layer was back extracted with toluene and the organic layers were dried over magnesium sulfate, filtered, and evaporated. Material was dissolved in toluene and added sodium sulfite solution and stirred. The layers were separated, the aqueous layer extracted with toluene and the combined organic layers were dried over magnesium sulfate, filtered, and evaporated. The residue was purified by column chromatography eluting with 0 to 100% ethyl acetate/hexanes. Obtained 8.8 g of material (72%).

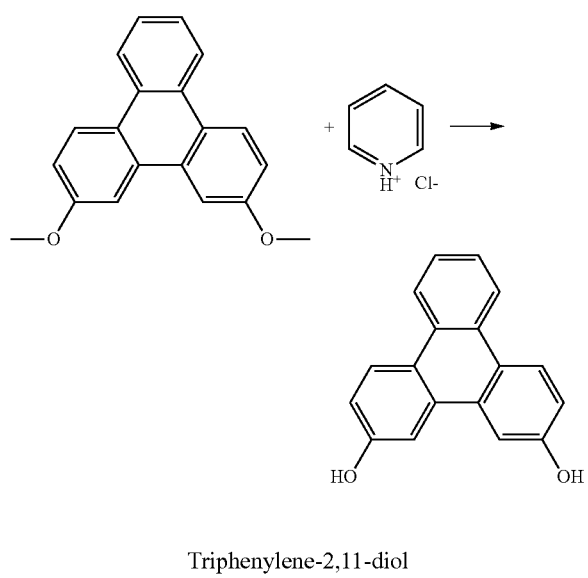

Triphenylene-2,11-diol

A mixture of 2,11-dimethoxytriphenylene (8.8 g, 30.5 mmol) and pyridine hydrochloride (31.73 g, 274.6 mmol) was heated to 220° C. for 2 hours. The mixture was cooled and water was added. The resulting solid was filtered off, washed with water, and dried under high vacuum. Obtained 7.45 g (94%) of desired product.

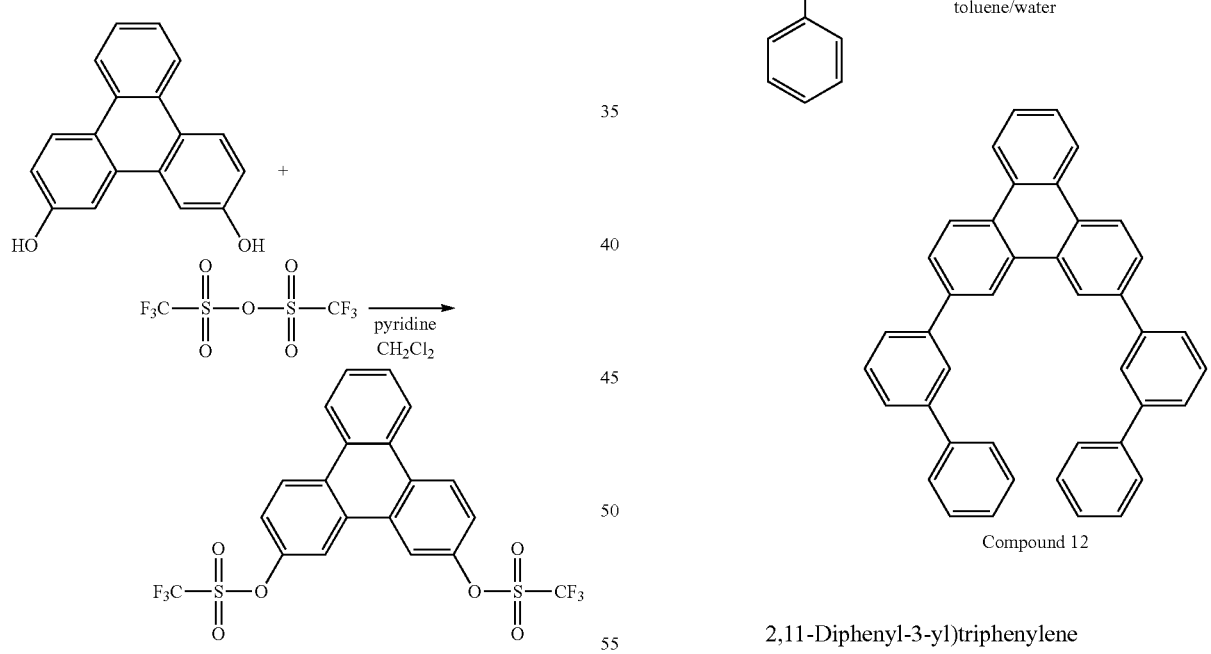

Triphenylene-2,11-dilyl bis(trifluoromethanesulfonate)

Triphenylene-2,11-diol (7.45 g, 28.62 mmol) was added to 100 mL dichloromethane and 13 mL pyridine and the solution was cooled in an ice salt bath. Trifluoromethanesulfonic anhydride (19 mL, 114.49 mmol) in 70 mL of dichloromethane was added dropwise to the solution under nitrogen. The reaction was allowed to proceed for 2 hours and quenched by adding by adding methanol and water followed by dilution with dichloromethane. A tan solid was filtered off and washed with dichloromethane and water. The layers in the filtrate were separated and the aqueous layer was extracted with dichloromethane. The organic extracts were dried over magnesium sulfate, filtered, and evaporated to yield a brown solid. The brown solid was purified by column chromatography eluting with 0 to 100% dichloromethane/hexanes. Obtained 1.8 g of desired product. The tan solid that was filtered in the work-up was purified by sublimation at 170° C. followed by recrystallization twice from 300 mL boiling toluene. Obtained 9.6 g of desired material, 11.4 g total (76%).

Compound 12

2,11-Diphenyl-3-yl)triphenylene

A mixture was prepared of triphenylene-2,11-dilyl bis(trifluoromethanesulfonate) (3.0 g, 5.72 mmol), 3-biphenylboronic acid (2.72 g 13.73 mmol), 2-dicyclohexylphosphino-2',6'-dimethoxybiphenyl (188 mg, 0.458 mmol), potassium phosphate tribasic (7.21 g, 34.32 mmol), toluene (120 mL), and water (50 mL). Nitrogen was bubbled directly in the solution for 30 minutes. Next tris(dibenzylideneacetone) dipalladium (0) (105 mg, 0.114 mmol) was added and the reaction mixture was heated to reflux overnight under nitrogen. The reaction mixture was cooled and a solid was filtered off and washed with water and methanol. The solid was dissolved in boiling toluene and filtered through magnesium sulfate. Material was isolated from the filtrate in the work-up. The combined material was purified by column chromatography eluting with 0 to 50% dichloromethane/hexanes, sublimation, column chromatography eluting with 20 and 30% dichloromethane/hexanes, recrystallization from dichloromethane/hexanes, and sublimation at 270° C. Obtained 1.5 g (50%) of pure product.

Synthesis of Comparative Example 3

4-Phenyl-1,2-dichlorobenzene

A mixture was prepared of 1-Bromo-3,4-dichlorobenzene (20.0 g, 88.5 mmol), phenylboronic acid (13.5 g, 110.6 mmol), triphenylphosphine (2.32 g, 8.85 mmol), potassium carbonate (30.58 g, 221.25 mmol), 150 mL xylenes, and 150 mL water. The mixture was stirred and nitrogen bubbled into it for 20 minutes. Palladium acetate was added (0.99 g, 4.425 mmol) and the mixture was heated at 120° C. under nitrogen overnight. Cooled to room temperature and diluted with water and dichloromethane. The mixture was filtered through Celite and the Celite was washed with water and dichloromethane. The layers were separated and the aqueous layer extracted with dichloromethane. The organic layers were dried over magnesium sulfate, filtered, and evaporated to yield a brown oil. The crude material was purified by column chromatography eluting with hexanes. The cleanest fractions containing product were collected. Obtained 6 g (30%) of clean product.

4-Phenyl-1,2-(4'-biphenyl)benzene

A mixture of 4-Phenyl-1,2-dichlorobenzene (6.0 g, 26.9 mmol), 4-biphenylboronic acid (13.3 g, 67.2 mmol), tris(dibenzylideneacetone)dipalladium(O) (739 mg, 0.807 mmol), potassium fluoride (6.95 g, 120.0 mmol), and 150 mL of THF was prepared. Nitrogen was bubbled through the mixture as it stirred for 15 minutes. Next, tri-t-butylphosphine was added (1M in toluene, 1.6 mL, 1.614 mmol) and the mixture refluxed overnight under nitrogen. The reaction was cooled to room temperature and filtered through Celite. The Celite was washed with dichloromethane and the filtrate was evaporated. The residue was taken up in dichloromethane and filtered off an insoluble grayish-white solid. The filtrate was purified by column chromatography eluting with dichloromethane/hexanes to yield 11.4 g (92%) of a white solid.

2,6,11-triphenyltriphenylene

A solution of 4-Phenyl-1,2-(4'-biphenyl)benzene (5 g, 10.90 mmol) in 150 mL dichloromethane was prepared and in cooled in a dry ice-acetone bath under nitrogen. To this solution, a solution of [Bis(trifluoroacetoxy)iodo]benzene (11.7 g, 27.26 mmol) and boron trifluoride diethyl ether (4.1 mL, 32.7 mmol) in 125 mL of dichloromethane was added dropwise. The reaction was stirred in the dry ice-acetone bath for 2 hours, and then warmed to 0° C. using an ice bath. The reaction was quenched with methanol and aqueous sodium sulfite solution and diluted with dichloromethane. The layers were separated and the aqueous layer was extracted with dichloromethane. The organic layers were dried over magnesium sulfate, filtered, and evaporated to a residue which was taken up in dichloromethane. An insoluble gray solid was filtered off. The filtrate was evaporated and purified by column chromatography eluting with dichloromethane/hexanes. The product was recrystallized from xylenes, and then sublimed at 250° C. The material was sublimed at 190° C. for 4 days to remove impurity, then purified by column chromatography eluting with 3:1 hexanes: dichloromethane to remove color. Lastly material was sublimed at 230° C. to obtain 0.98 g (20%) of a white solid.

Synthesis of Comparative Example 4

1,2-(4'-biphenyl)benzene

To a 1-L 3-necked round-bottom flask was added 1,2-dibromobenzene (25 g, 106 mmol), 4-biphenylboronic acid (52.5 g, 265 mmol), triphenylphosphine (5.6 g, 21.2 mmol), potassium carbonate (36.6 g, 265 mmol), 160 mL DME, and 160 mL water. Nitrogen was bubbled into mixture for 30 minutes, and then palladium acetate (2.4 g, 10.6 mmol) was added. The reaction mixture was refluxed overnight under nitrogen. The reaction mixture was cooled to room temperature. A black solid was collected and washed with water, then dried to yield 54.1 g. A portion (15.2 g) was purified by column chromatography eluting with dichloromethane/hexanes followed by recrystallization from toluene/hexanes.

2,11-diphenyltriphenylene

A solution of 1,2-(4'-biphenyl)benzene (4.44 g, 11.61 mmol) in 110 mL dichloromethane was prepared and in cooled in a dry ice-acetone bath under nitrogen. To this solution, a solution of [Bis(trifluoroacetoxy)iodo]benzene (12.73 g, 29.6 mmol) and boron trifluoride diethyl ether (4.4 mL, 34.83 mmol) in 100 mL of dichloromethane was added dropwise. The reaction was stirred in the dry ice-acetone bath for 2 hours, and then warmed to 0° C. using an ice-salt bath. The reaction was quenched with methanol and aqueous sodium sulfite solution and diluted with dichloromethane. An emulsion resulted; the mixture was then filtered through Celite. The layers were separated and the aqueous layer was extracted with dichloromethane. The organic layers were washed with brine, dried over magnesium sulfate, filtered, evaporated to a residue. The residue was purified by column chromatography twice eluting with dichloromethane/hexanes followed by sublimation at 210° C. Obtained 0.51 g (12%) of a white solid.

VTE Device Data:

Devices 1-9 were fabricated on 1200 Å thick ITO using high vacuum thermal evaporation (VTE). All devices were fabricated using the following device structure and layer thicknesses: ITO/HIL(100 Å)/HTL(300 Å)/EML(300 Å)/ETL2(50 Å)/ETL1(450 Å)/LiF/Al. These layers are defined as follows: HIL is the hole injection layer, HTL is the hole transport layer, EML is the doped emissive layer, ETL2 is the enhancement layer and ETL is the electron transport layer. All devices were fabricated with an HIL comprised of dopant 1, an HTL of NPD and an ETL of $Alq_3$. The EML were comprised of various single triphenylene hosts doped at 10 wt % with the green emissive dopant 1. The BL used were either HPT or the triphenylene containing host. A 10 Å thick layer of LiF followed by a 1000 Å thick layer of Al was used as the cathode. All devices were lifetested at a constant current density of 40 mA/cm$^2$. The characteristics of the VTE devices are shown in Table 1 and FIGS. 3-8.

Device 1: ITO/dopant 1/NPD/Compound 1:dopant 1 (10%)/Compound 1/$Alq_3$/LiF/Al

Device 2: ITO/dopant 1/NPD/Compound 2:dopant 1 (10%)/Compound 2/$Alq_3$LiF/Al

Device 3: ITO/dopant 1/NPD/Compound 4:dopant 1 (10%)/Compound 4/Alq$_3$/LiF/Al
Device 4: ITO/dopant 1/NPD/Compound 7:dopant 1 (10%)/HPT/Alq$_3$/LiF/Al
Device 5: ITO/dopant 1/NPD/Compound 8:dopant 1 (10%)/HPT/Alq$_3$/LiF/Al
Device 6: ITO/dopant 1/NPD/Compound 11:dopant 1 (10%)/HPT/Alq$_3$/LiF/Al
Device 7: ITO/dopant 1/NPD/Comparative example 1:dopant 1 (10%)/HPT/Alq$_3$/LiF/Al
Device 8: ITO/dopant 1/NPD/Comparative example 3:dopant 1 (10%)/comparative example 3/Alq$_3$/LiF/Al
Device 9: ITO/dopant 1/NPD/Comparative example 4:dopant 1 (10%)/comparative example 4/Alq$_3$/LiF/Al Material Definitions:
Dopant 1 and HPT have the following structures:

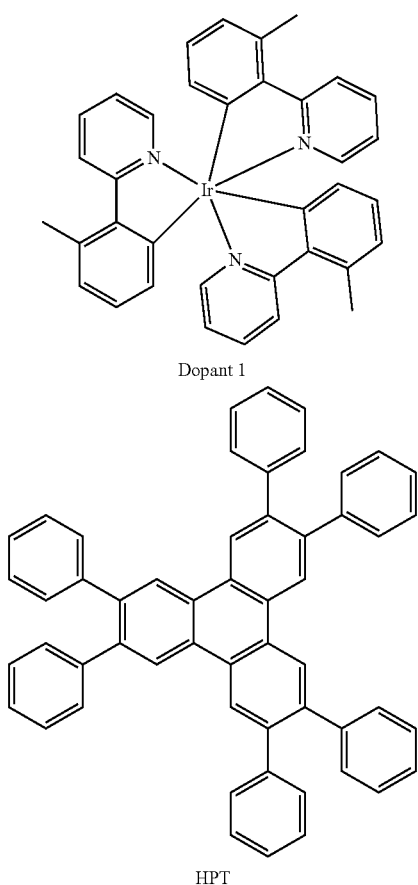

Dopant 1

HPT

TABLE 1

The CIE spectra for devices 1-9

|  | x | y |
|---|---|---|
| Device 1 | 0.352 | 0.610 |
| Device 2 | 0.344 | 0.614 |
| Device 3 | 0.347 | 0.613 |
| Device 4 | 0.357 | 0.606 |
| Device 5 | 0.354 | 0.607 |
| Device 6 | 0.350 | 0.612 |
| Device 7 | 0.367 | 0.600 |
| Device 8 | 0.359 | 0.598 |
| Device 9 | 0.357 | 0.608 |

Solution Processed Device Data:

Devices 10-15 were fabricated using a solution process as follows: The hole injection layer was spin-coated from a 0.25 wt % solution of the HIL and the dopant trityl-tetrakis (pentafluorophenyl)borate (CD1) in cyclohexanone at 4000 rpm for 30 seconds. The film was baked at 250° C. for 30 min. For the hole transport layer, a 1.0 wt % solution of N4,N4'-di(naphthalen-1-yl)-N4,N4'-bis(4-vinylphenyl)biphenyl-4,4'-diamine in toluene was spin-coated onto the hole injection layer at 4000 rpm for 30 seconds. The film was then baked at 200° C. for 30 minutes on a hot plate in a glovebox. The film became insoluble after baking. After cooling to room temperature, the emissive layer was deposited by spin-coating a solution of 0.75 wt % host and dopant 2 (host to dopant ratio: 88:12) onto the hole transport layer at 1000 rpm for 30 seconds. The emissive layer was then baked at 100° C. for one hour. A 5 nm thick layer of 2,3,6,7,10,11-hexaphenyltriphenylene (HPT) and a 50 nm thick layer of Alq$_3$ were subsequently deposited by vacuum thermal evaporation followed by a LiF/Al cathode.

TABLE 2

| Device # | HIL | EML | Voltage (@ 1000 nits) | Luminous efficiency (@ 1000 nits) | Lifetime (hr) (80% L$_0$ = 4000 nits) |
|---|---|---|---|---|---|
| 10 | HIL1: CD1 (3%) | Compound 1: dopant 2 | 8.0 | 46 | 180 |
| 11 | HIL1: CD1 (7%) | Compound 1: dopant 2 | 7.4 | 50 | 120 |
| 12 | HIL2: CD1 (5%) | Compound 2: dopant 2 | 7.8 | 46 | 87 |
| 13 | HIL3: CD1 (5%) | Compound 2: dopant 2 | 10.2 | 25 | 700 |

TABLE 2-continued
| Device # | HIL | EML | Voltage (@ 1000 nits) | Luminous efficiency (@ 1000 nits) | Lifetime (hr) (80% L$_0$ = 4000 nits) |
|---|---|---|---|---|---|
| 14 | HIL4: CD1 (5%) | Compound 2: dopant 2 | 8 | 44 | 130 |
| 15 | HIL5: CD1 (10%) | Compound 4: dopant 2 | 7.9 | 50 | 208 |
Material Definitions
G1
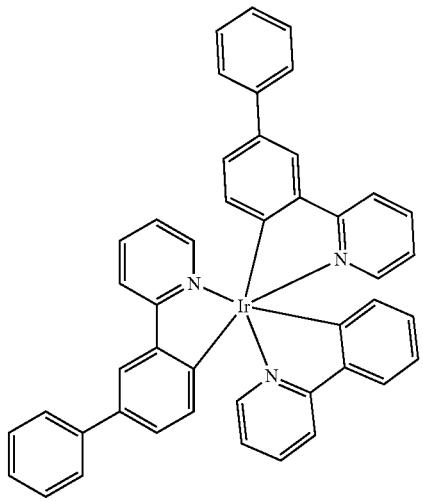
G3
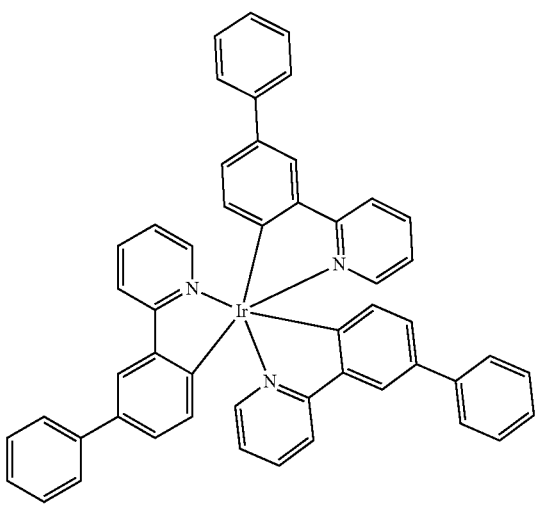
G4
Dopant 2: A mixture of compounds G1, G2, G3, and G4 in a ratio of 2:37:53:7.

CD1
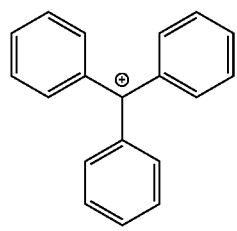 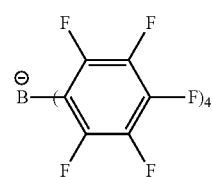
HIL1
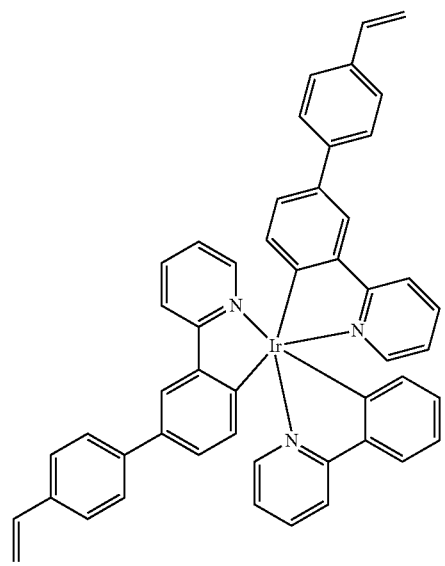
HIL2
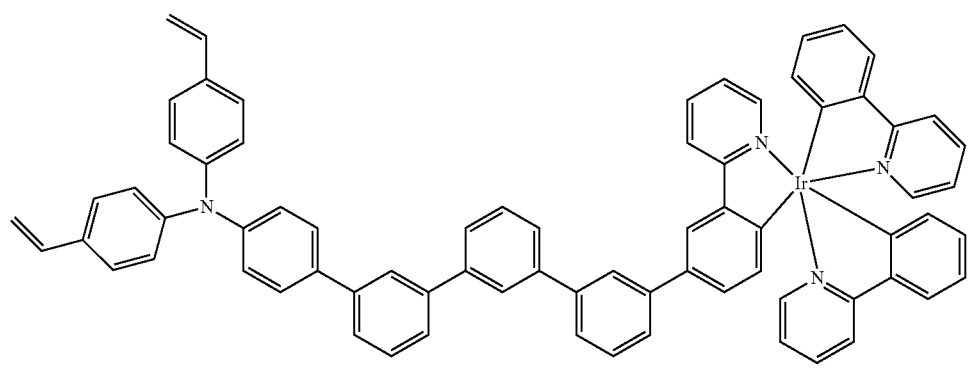
HIL3
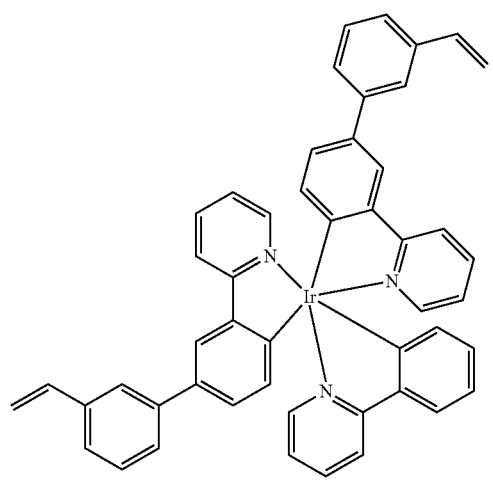
HIL4
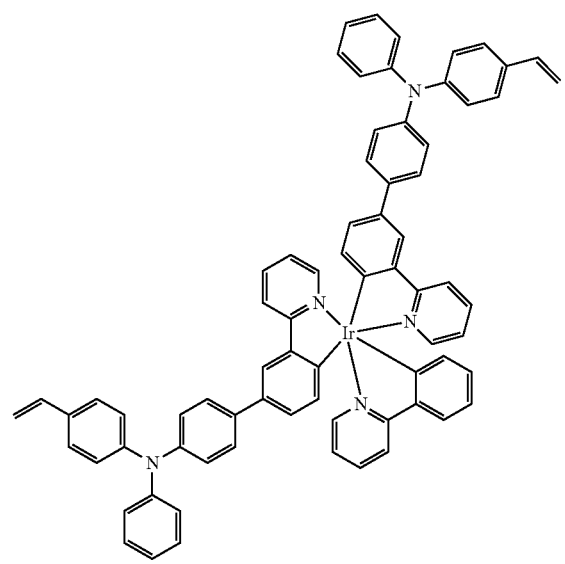

-continued

HIL5

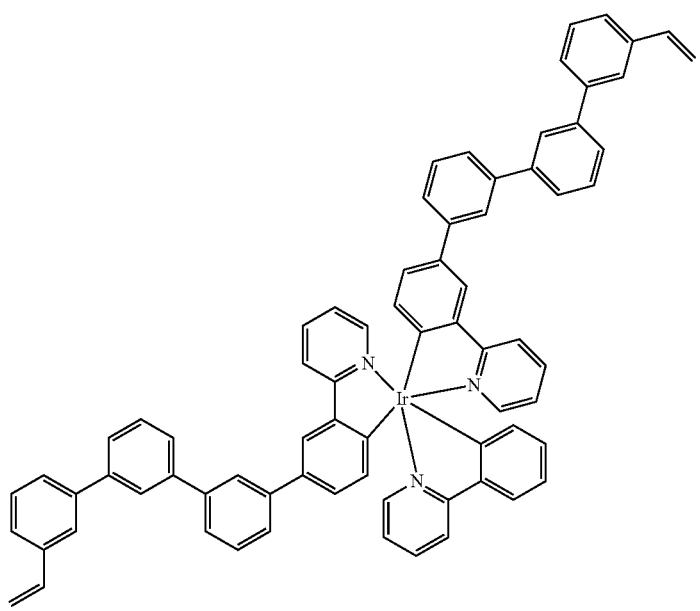

Phosphorescent devices with very high device efficiency are highly desirable in applications such as display, lighting, etc. For full color and lighting application, high operational stability in red, green and blue colors is essential. Due to the high triplet energy nature of blue phosphorescent dopant emitters, high triplet energy host materials are required so that high device efficiency can be obtained. In OLEDs, polyaromatic compounds with extended it-conjugation usually show respectable lifetimes. However, polyaromatic compounds with extended it-conjugation usually have low triplet energy also. For example, anthracene has a triplet energy of 1.8 eV which is lower than those of red phosphorescent dopants such as $Ir(1\text{-piq})_2(acac)$. As a result, a device with an anthracene compound as the host with $Ir(1\text{-piq})_2$ (acac) as the dopant emitter is very inefficient, because of quenching. Reducing one fused phenyl ring from anthracene gives naphthalene which is the smallest fused polyaromatic compound. Yet it still has a triplet energy of 2.6 eV which is lower than those of deep blue phosphorescent dopants such as $Ir(4,6\text{-}F_2\text{-5CNppy})_3$. However, triphenylene, despite its four fused ring configuration, has a triplet energy of 2.9 eV which is believed to be suitable for deep blue phosphorescent dopants such as $Ir(4,6\text{-}F_2\text{-5CNppy})_3$. Triphenylene can be derivatized in various ways such as adding alkyl or aryl groups, linking multiple or fusing triphenylenes through different positions to modulate the electronic properties (e.g. conjugation, triplet energy, HOMO/LUMO levels, etc), structure properties (e.g., planar, non-planar, chirality), and physical properties (e.g., sublimation temperature, solubility). The unique property that triphenylene compounds provides relatively large degree of it-conjugation but relatively high triplet energy renders them very suitable for stable and high-efficiency PHOLEDs.

It is understood that the various embodiments described herein are by way of example only, and are not intended to limit the scope of the invention. For example, the non-fused aryl group having one or more meta-substituents may be attached to a triphenylene at any position. Many of the materials and structures described herein may be substituted with other materials and structures without deviating from the spirit of the invention. It is understood that various theories as to why the invention works are not intended to be limiting.

What is claimed is:

1. A compound comprising a triphenylene core of Formula F:

F

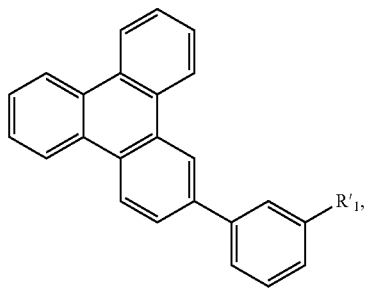

wherein $R'_1$ is a non-fused aryl group substituted with $R_a$, wherein $R_a$ is selected from a non-fused aryl or heteroaryl, a branched or straight chain of non-fused aryls or heteroaryls, and alkyl substituted aryl or heteroaryl group.

2. The compound of claim 1, wherein the compound is:

Compound 9

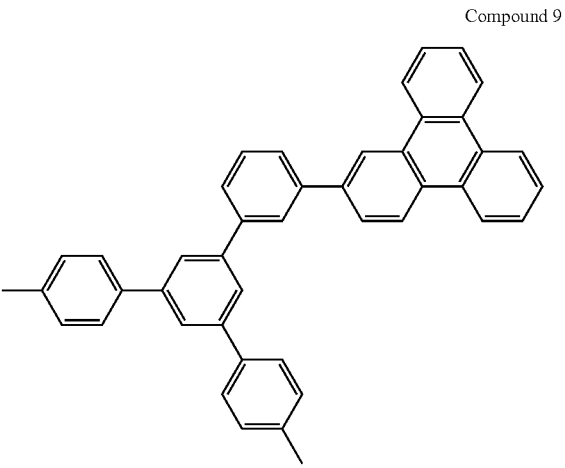

-continued

Compound 10

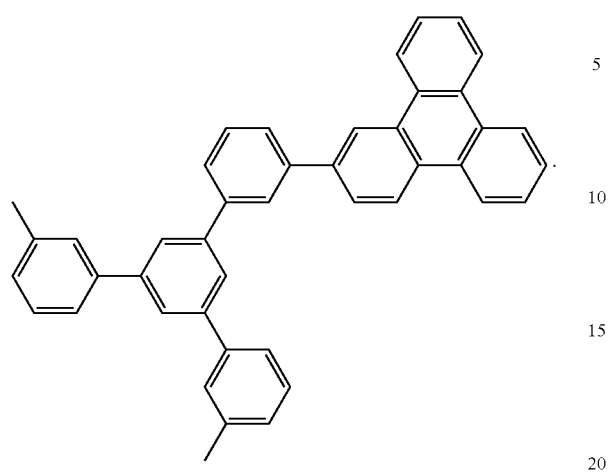

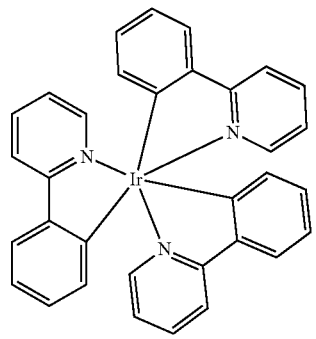
G1

3. The compound of claim 1, having no more than three para-substituted phenyl rings including the phenyl rings of the triphenylene core.

4. An organic light emitting device, comprising:
   an anode;
   a cathode;
   an organic layer, disposed between the anode and the cathode, wherein the organic layer comprises a compound comprising a triphenylene core of Formula F:

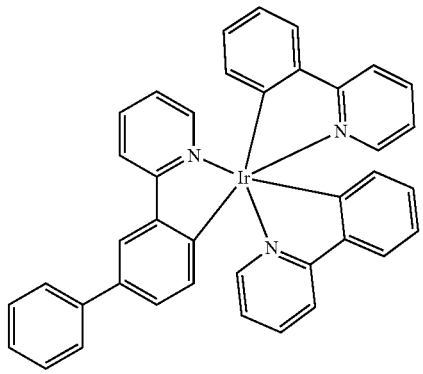
G2

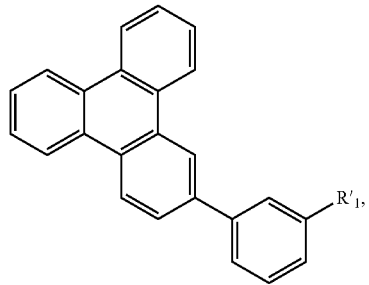
F wherein $R'_1$ is a non-fused aryl group substituted with $R_a$, wherein $R_a$ is selected from a non-fused aryl or heteroaryl, a branched or straight chain of non-fused aryls or heteroaryls, and alkyl substituted aryl or heteroaryl group.

5. The organic light emitting device of claim 4, wherein the organic layer is an emitting layer having a host and an emissive dopant, and the compound is the host.

6. The organic light emitting device of claim 5, wherein the emissive dopant is phosphorescent.

7. The organic light emitting device of claim 5, wherein the emissive dopant is selected from the group consisting of:

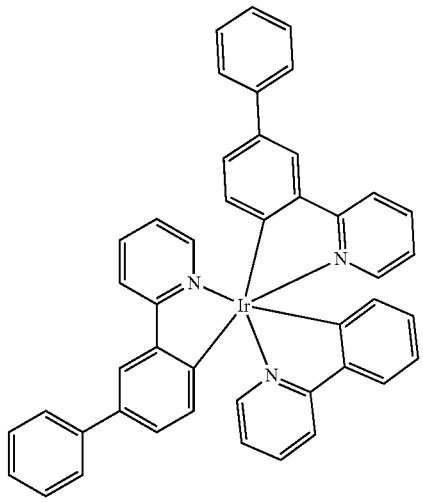
G3

-continued

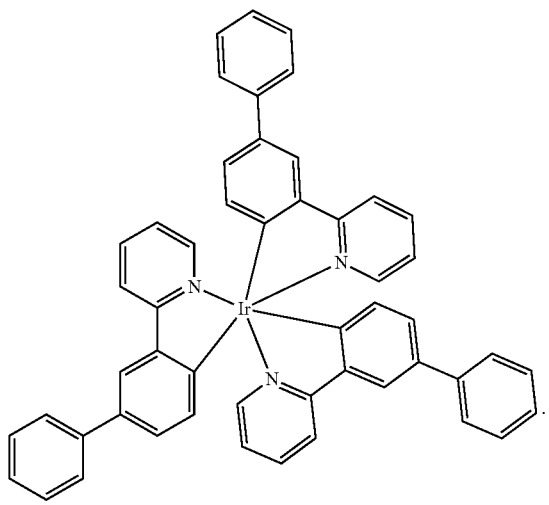

G4

8. A consumer product comprising an organic light emitting device (OLED), comprising:
   an anode;
   a cathode;
   an organic layer, disposed between the anode and the cathode, wherein the organic layer comprises a compound comprising a triphenylene core of Formula F:

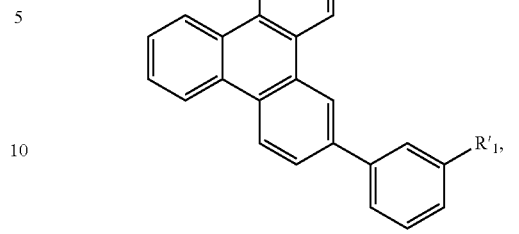

F wherein $R'_1$ is a non-fused aryl group substituted with $R_a$, wherein $R_a$ is selected from a non-fused aryl or heteroaryl, a branched or straight chain of non-fused aryls or heteroaryls, and alkyl substituted aryl or heteroaryl group.

9. The consumer product of claim 8, wherein the consumer product is selected from the group consisting of a flat panel display, a computer monitor, a television, a billboard, lights for interior or exterior illumination and/or signaling, a heads up display, a fully transparent display, a flexible display, a laser printer, a telephone, a cell phone, a personal digital assistant (PDA), a laptop computer, a digital camera, a camcorder, a viewfinder, a vehicle, a wall, theater or stadium screen, and a sign.

* * * * *